(12) United States Patent
Samarev et al.

(10) Patent No.: US 11,068,917 B2
(45) Date of Patent: Jul. 20, 2021

(54) PREDICTION OF BUSINESS OUTCOMES BY ANALYZING IMAGE INTERESTS OF USERS

(71) Applicant: DOTIN INC., San Jose, CA (US)

(72) Inventors: Roman Samarev, San Jose, CA (US); Ganesh Iyer, San Jose, CA (US)

(73) Assignee: DOTIN INC., San Jose, CA (US)

( * ) Notice: Subject to any disclaimer, the term of this patent is extended or adjusted under 35 U.S.C. 154(b) by 154 days.

(21) Appl. No.: 16/213,191

(22) Filed: Dec. 7, 2018

(65) Prior Publication Data

US 2020/0184495 A1 Jun. 11, 2020

(51) Int. Cl.

| | |
|---|---|
| G06Q 30/00 | (2012.01) |
| G06Q 30/02 | (2012.01) |
| A61B 5/16 | (2006.01) |
| G06N 3/08 | (2006.01) |
| G06K 9/46 | (2006.01) |
| G06K 9/72 | (2006.01) |
| G10L 15/02 | (2006.01) |
| G10L 15/08 | (2006.01) |
| G06F 40/56 | (2020.01) |
| G06F 40/40 | (2020.01) |
| G06F 16/2457 | (2019.01) |

(Continued)

(52) U.S. Cl.
CPC ........... G06Q 30/0202 (2013.01); A61B 5/16 (2013.01); G06F 3/04842 (2013.01); G06F 16/24578 (2019.01); G06F 16/90324 (2019.01); G06F 40/40 (2020.01); G06F 40/56 (2020.01); G06K 9/46 (2013.01); G06K 9/4652 (2013.01); G06K 9/726 (2013.01); G06N 3/08 (2013.01); G10L 15/02 (2013.01); G10L 15/083 (2013.01)

(58) Field of Classification Search
None
See application file for complete search history.

(56) References Cited

U.S. PATENT DOCUMENTS 7,885,902 B1 * 2/2011 Shoemaker ............ G06Q 10/10
705/319
8,200,527 B1 * 6/2012 Thompson ....... G06Q 10/06398
705/7.39

(Continued)

OTHER PUBLICATIONS

Day, J. (2003). The relationship of the business with the in-house IT department: A customer-provider perspective (Order No. 10694424). Available from ProQuest Dissertations and Theses Professional (Year: 2003).*

(Continued)

Primary Examiner — Gurkanwaljit Singh
(74) Attorney, Agent, or Firm — Chip Law Group

(57) ABSTRACT

A method and a system for predicting business outcomes by analyzing image interests of users are provided. The method includes generation of predictor models based on sample data of tests users. The sample data includes historical data of the test users, images that are of interest to the test users, and answers provided by the test users to psychometric questions. The predictor models are then used to predict psychometric features and business outcomes for a target user based on target data of the target user. The target data includes images that are of interest to the target user, historical data of the target user, and answers provided by the target user to the psychometric questions.

19 Claims, 16 Drawing Sheets

(51) Int. Cl.
*G06F 3/0484* (2013.01)
*G06F 16/9032* (2019.01)

(56) References Cited

U.S. PATENT DOCUMENTS

| | | | | |
|---|---|---|---|---|
| 8,204,809 | B1* | 6/2012 | Wise | G06Q 40/06 705/35 |
| 8,214,238 | B1* | 7/2012 | Fairfield | G06Q 10/0639 705/7.11 |
| 8,311,863 | B1* | 11/2012 | Kemp | G06Q 10/0639 705/7.11 |
| 8,417,715 | B1* | 4/2013 | Bruckhaus | G06Q 30/0202 707/758 |
| 9,396,483 | B2* | 7/2016 | Hamedi | G06Q 50/01 |
| 10,020,076 | B1* | 7/2018 | Anumalasetty | G16H 10/60 |
| 2003/0130884 | A1* | 7/2003 | Michaluk | G06Q 10/06393 705/7.36 |
| 2004/0210661 | A1* | 10/2004 | Thompson | G06Q 30/02 709/228 |
| 2007/0050215 | A1* | 3/2007 | Kil | G16H 50/30 705/3 |
| 2007/0094060 | A1* | 4/2007 | Apps | G06F 16/2465 705/7.36 |
| 2008/0015871 | A1* | 1/2008 | Eder | G06Q 10/067 706/21 |
| 2009/0018891 | A1* | 1/2009 | Eder | G06Q 10/06375 705/7.28 |
| 2009/0254971 | A1* | 10/2009 | Herz | G06Q 30/0603 726/1 |
| 2009/0327068 | A1* | 12/2009 | Pradeep | G06Q 30/0244 705/14.43 |
| 2011/0020778 | A1* | 1/2011 | Forbes | G16H 20/70 434/236 |
| 2013/0339099 | A1* | 12/2013 | Aidroos | G06Q 10/0637 705/7.36 |
| 2014/0058794 | A1* | 2/2014 | Malov | G06Q 10/083 705/7.31 |
| 2014/0214709 | A1* | 7/2014 | Greaney | G06Q 10/1053 705/321 |
| 2016/0078471 | A1* | 3/2016 | Hamedi | H04L 67/1072 705/14.41 |
| 2016/0080485 | A1* | 3/2016 | Hamedi | G06Q 30/0242 709/204 |
| 2017/0188976 | A1* | 7/2017 | Kalra | G16H 10/20 |
| 2017/0193533 | A1 | 7/2017 | Lai et al. | |
| 2017/0287473 | A1* | 10/2017 | Levanon | G10L 25/63 |
| 2019/0034976 | A1* | 1/2019 | Hamedi | G06Q 30/0204 |

OTHER PUBLICATIONS

Edersen, M. (2013). A quantitative examination of critical success factors comparing agile and waterfall project management methodologies (Order No. 3602588). Available from ProQuest Dissertations and Theses Professional (Year: 2013).*

Cap, I. (1995). A study of the usefulness and effectiveness of a self-instructional print module on multicultural behaviour change in apprentices in manitoba (Order No. 9525912). Available from ProQuest Dissertations and Theses Professional (Year: 1995).*

* cited by examiner

PREDICTION OF BUSINESS OUTCOMES BY ANALYZING IMAGE INTERESTS OF USERS

FIELD

Various embodiments of the disclosure relate generally to business enhancement using machine learning. More specifically, various embodiments of the disclosure relate to prediction of business outcomes by analyzing image interests of users.

BACKGROUND

There are always risks associated with initiating new endeavors, especially in a business. The severity of these risks, however, may be substantially minimized if potential outcomes, both positive and negative, are predicted. For an individual, it may include getting suggestion for a suitable job profile, while for an organization, such as an e-commerce service provider, it may include identifying purchase behavior of customers to suitably adjust their inventory to target the customers. Likewise, for increasing work productivity and efficiency of employees, a business organization may determine job affinity of the employees and accordingly allocate different work profiles and tasks to the employees.

Psychometric analysis plays an important role in identifying the potential business outcomes for users and organizations. A known technique of psychometric analysis includes interviewing, where an interviewer may have a close interaction with an interviewee and observe conscious, subconscious, and semiconscious behavior of the interviewee. Generally, interviewing is more focused on personal judgement of the interviewer. However, personal judgement, even that of an expert, has no guarantee of being reliable and meaningful in actual practice. Another known technique of psychometric analysis involves analyzing psychosocial reactions of users to artificially created situations, such as Thematic Apperception Test (TAT), Word Association Test (WAT), and the like. However, such tests fail to consider recent activities and behavioural changes of the users for psychometric analysis, thus making the results of psychometric analysis less accurate.

In light of the foregoing, there exists a need for a solution that overcomes aforementioned problems and provides accurate business outcomes.

Further limitations and disadvantages of conventional and traditional approaches will become apparent to one of skill in the art, through comparison of described systems with some aspects of the present disclosure, as set forth in the remainder of the present application and with reference to the drawings.

SUMMARY

Prediction of business outcomes by analyzing image interests of users is provided substantially as shown in, and described in connection with, at least one of the figures, as set forth more completely in the claims.

These and other features and advantages of the disclosure may be appreciated from a review of the following detailed description of the disclosure, along with the accompanying figures in which like reference numerals refer to like parts throughout.

DETAILED DESCRIPTION

Figure 1:
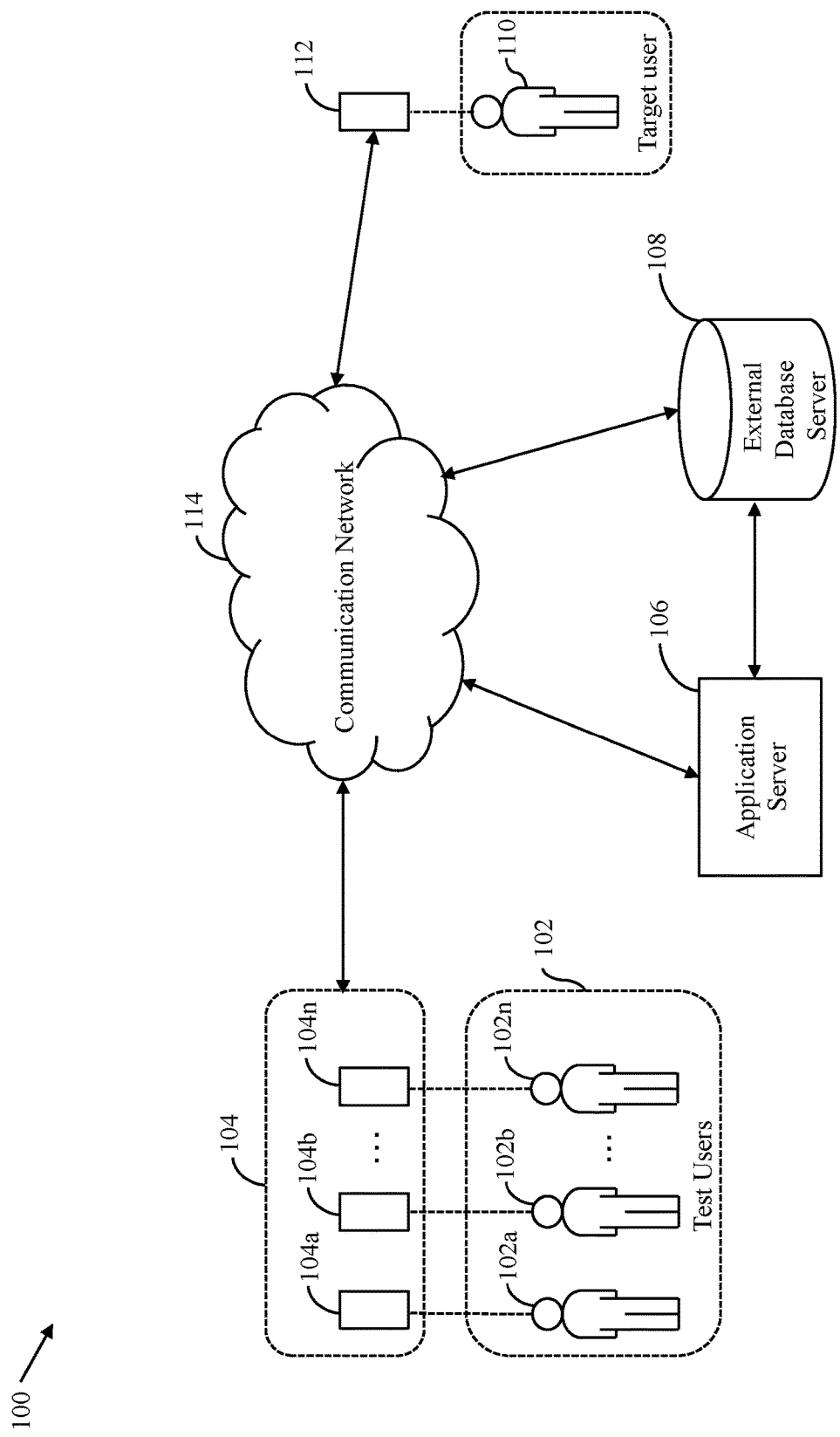
FIG. 1 is a block diagram that illustrates an exemplary environment for prediction of business outcomes by analyzing image interests of users, in accordance with an embodiment of the disclosure.

Certain embodiments of the disclosure may be found in a disclosed apparatus for predicting business outcomes by analyzing image interests of users. Exemplary aspects of the disclosure provide methods and systems for predicting business outcomes for users. The method includes retrieving, by a server, historical data of at least one test user, a first set of images that is of interest to the test user, and a first set of answers provided by the test user to a set of psychometric questions. The first set of answers and the first set of images are analyzed by the server. The server may be configured to analyze the first set of answers for deriving one or more psychometric features of the test user. The server may be configured to analyze the first set of images for extracting a first set of feature values corresponding to a set of image features from the first set of images. Each image feature of the set of image features is independent of one or more objects associated with the first set of images. One or more predictor models are generated by the server based on the historical data of the test user, the first set of feature values, and the one or more psychometric features of the test user. One or more business outcomes for a target user may be predicted by the server based on the one or more predictor models and a second set of images that is of interest to the target user.

Another embodiment provides the system for predicting business outcomes for users. The system includes a server that may be configured to retrieve historical data of at least one test user, a first set of images that is of interest to the test user, and a first set of answers provided by the test user to a set of psychometric questions. The server may be configured to analyze the first set of answers and the first set of images. The first set of answers is analyzed for deriving one or more psychometric features of the test user. The first set of images is analyzed for extracting a first set of feature values corresponding to a set of image features from the first set of images. Each image feature of the set of image features is independent of one or more objects associated with the first set of images. The server may be configured to generate one or more predictor models based on the historical data of the test user, the first set of feature values, and the one or more psychometric features of the test user. The server may be configured to predict one or more business outcomes for a target user based on the one or more predictor models and a second set of images that is of interest to the target user.

The disclosure includes the prediction of business outcomes by analyzing images that accurately reflect one's subconscious mind. As the subconscious mind is responsible for a majority of decision-making tasks and is directly related to an individual's personality, the disclosure yields more accurate results in comparison to related techniques. Moreover, the behavioral changes of an individual are directly reflected by the choice of images made by the individual. For example, a person's liking towards a particular image may vary based on an emotional state of the person. In one exemplary scenario, the predicted business outcomes may be used by an organization for improving marketing strategies and in turn expanding business. For example, the organization may target a specific group of customers for advertising a newly launched product when the customers in the group have high product purchase affinity (i.e., a business outcome) for the launched product. In another exemplary scenario, the predicted business outcomes may be used by an organization to simplify resource management. For example, E-commerce industries may use the predicted business outcomes (such as predicted inventory requirements) to manage their inventory. Likewise, airline industry may use the predicted business outcomes to customize ticket prices to attract more customers.

FIG. 1 is a block diagram that illustrates an exemplary environment 100 for prediction of business outcomes by analyzing image interests of users, in accordance with an embodiment of the disclosure. The environment 100 includes test users 102a-102n (hereinafter designated and referred to as "the test users 102"), test-user devices 104a-104n (hereinafter designated and referred to as "the test-user devices 104"), an application server 106, and an external database server 108. The environment 100 further includes a target user 110 and a target-user device 112. The test-user devices 104, the application server 106, the external database server 108, and the target-user device 112 may communicate with each other by way of a communication network 114 or any other communication means established therebetween.

The test users 102 are individuals, whose sample data may be used to generate predictor models for predicting business outcomes for the target user 110. The sample data of the test users 102 may include historical data of the corresponding test users 102, images that are of interest to the corresponding test users 102, and answers provided by the corresponding test users 102 to various psychometric questions. The historical data of the test users 102 may refer to data collected based on past events pertaining to the test users 102. The historical data may include data generated either manually or automatically by the test users 102. For example, the historical data of the test user 102a may include curriculum information, education particulars, travel history, activity on social media platforms, employment details, and purchase history of the test user 102a. The historical data of the test user 102a may further include an activity log of the test user 102a on the internet and various social media platforms. The answers to the psychometric questions may be provided by the test user 102a when the psychometric questions are presented to the test user 102a through various online tests (such as, but not limited to, the multiple intelligence quiz, the BIG 5, or the personal globe inventory) on the test-user device 104a. The images that are of interest to the test user 102a may include images viewed by the test user 102a through the internet, images liked and shared by the test user 102a on the social media platforms, and images stored in a memory of the test-user device 104a.

The test-user devices 104 may include suitable logic, circuitry, interfaces, and/or code, executable by the circuitry, that may be configured to perform one or more operations for providing the sample data of the test users 102a-102n to the application server 106. In one exemplary scenario, the test-user devices 104 may refer to communication devices of the test users 102. The test-user devices 104 may be configured to allow the test users 102 to communicate with the application server 106 and the external database server 108. The test-user devices 104 may be configured to serve as an interface for providing the sample data of the corresponding test users 102 to the application server 106. In one embodiment, the test-user device 104a may be configured to run or execute a software application (e.g. a mobile application or a web application), which may be hosted by the application server 106, for presenting various images and psychometric questions to the test user 102a, and communicating a response of the test user 102a to the application server 106. The response may include a list of images from the presented images that are liked by the test user 102a and the answers provided by the test user 102a to the psychometric questions. The test-user device 104a may be further configured to obtain a consent of the test user 102a for accessing and communicating various images stored in the memory of the test-user device 104a. Based on the consent of the test user 102a, the test-user device 104a may be configured to keep a track of the images liked, followed, and/or shared by the test user 102a on the internet and the social media platforms. The test-user device 104a may be further configured to retrieve the historical data of the test user 102a by accessing a social media profile of the test user 102a based on the consent of the test user 102a. Likewise, the test-user devices 104b-104n of the other test users 102b-102n may be configured to provide the sample data of the other test users 102b-102n to the application server 106. Examples of the test-user devices 104 may include, but are not limited to, mobile phones, smartphones, laptops, tablets, phablets, or other devices capable of communicating via the communication network 114.

The application server 106 may include suitable logic, circuitry, interfaces, and/or code, executable by the circuitry, that may be configured to perform one or more operations for predicting business outcomes. The application server 106 may be a physical or cloud data processing system on which a server program runs. The application server 106 may be implemented in hardware or software, or a combination thereof. The application server 106 may be configured to host the software application which may be accessible on the internet for providing a personality and business outcomes prediction service. The application server 106 may be configured to utilize the software application for retrieving the sample data of the test users 102. The application server 106 may be further configured to use a tracker or a web crawler to track the activities of the test users 102 on the internet and the social media platforms for retrieving the sample data.

The application server 106 may be configured to implement a learning phase based on the sample data for generating the predictor models. The predictor models may be statistical models generated by means of machine learning algorithms. Examples of the algorithms used for generating the predictor models may include, but are not limited to, a Support Vector Machine (SVM), a Logistic Regression model, a Bayesian Classifier model, a Decision Tree Classifier, a Copula-based Classifier, a K-Nearest Neighbors (KNN) Classifier, a Random Forest (RF) Classifier, or Artificial neural networks.

After the generation of the predictor models, the application server 106 may be configured to implement a prediction phase in which the predictor models are used to predict the business outcomes for the target user 110 based on various inputs received from the target user 110 (hereinafter the inputs received from the target user 110 are designated and referred to as "the target data"). In one embodiment, the business outcomes may include employment suggestions, compatibility match, product purchase affinity, color affinity, work affinity, image suggestions, and/or the like. In another embodiment, the business outcomes may include work affinity of employees, inventory suggestions, travel trend, purchase trend, and/or the like. Examples of the application server 106, include, but are not limited to, computers, laptops, mini-computers, mainframe computers, any non-transient and tangible machines that may execute a machine-readable code, a cloud-based server, or a network of computer systems. The application server 106 may be realized through various web-based technologies, such as, but not limited to, a Java web-framework, a .NET framework, a PHP framework, or any other web-application framework.

Various functional elements of the application server 106 have been described in detail in conjunction with FIG. 2 and generation of the predictor models is described later in FIG. 3.

The external database server 108 may include suitable logic, circuitry, interfaces, and/or code, executable by the circuitry, that may be configured to perform one or more operations for managing and storing various forms of data. In one embodiment, the external database server 108 may be implemented as a local memory of the application server 106. In another embodiment, the external database server 108 may be implemented as a cloud-based server working in conjunction with the application server 106. The external database server 108 may be configured to store data, such as the sample data provided the test users 102, the target data retrieved from the target user 110, and the predictor models generated by the application server 106. The external database server 108 may be configured to receive a query from the application server 106 to extract data stored in the memory of the external database server 108. Based on the received query, the external database server 108 may be configured to provide the requested data to the application server 106 over the communication network 114. Examples of the external database server 108 may include, but are not limited to, MySQL® and Oracle®.

The target user 110 may be an individual, whose target data may be used as input to the predictor models for predicting the business outcomes. In one exemplary scenario, the target user 110 may be an individual interested in determining a compatibility match or an individual seeking suggestion regarding employment. In another exemplary scenario, the target user 110 may be a representative of an organization who wants to know future business outcomes pertaining to a new policy implementation. In another exemplary scenario, the target user 110 may be an employee of the organization, whose employment affinity (i.e., a business outcome) is of interest to the organization. In another exemplary scenario, the target user 110 may be a customer whose purchase behavior is of interest to a business industry, such as an e-commerce industry. The target data may include various images that are of interest to the target user 110, answers provided by the target user 110 to the psychometric questions, and/or historical data of the target user 110. The application server 106 may be configured to obtain the target data in a manner that is similar to obtaining the sample data of the test users 102.

The target-user device 112 may include suitable logic, circuitry, interfaces, and/or code, executable by the circuitry, that may be configured to perform one or more operations for providing the target data of the target user 110 to the application server 106. In one exemplary scenario, the target-user device 112 may refer to a communication device of the target user 110. The target-user device 112 may be configured to allow the target user 110 to communicate with the application server 106 and the external database server 108. The target-user device 112 may be configured to provide the target data to the application server 106. In an exemplary scenario, the target-user device 112 may be configured to run or execute the software application, which is hosted by the application server 106, for retrieving the images that are of interest to the target user 110 and presenting various psychometric questions to the target user 110 for answering. The target-user device 112 may be further configured to communicate response of the target user 110 and the retrieved images to the application server 106. The response may include the answers provided by the target user 110 to the psychometric questions. Based on a consent of the target user 110, the target-user device 112 may be configured to access and communicate various images stored in the memory of the target-user device 112 to the application server 106. The target-user device 112 may be further configured to retrieve, with the consent of the target user 110, images liked, followed, and/or shared by the target user 110 on the internet and the social media platforms and communicate the retrieved images to the application server 106. The target-user device 112 may be further configured to retrieve the historical data of the target user 110 by accessing a social media profile of the target user 110 based on a consent of the target user 110 and provide the retrieved historical data to the application server 106. Examples of the target-user device 112 include, but are not limited to, a mobile phone, a smartphone, a laptop, a tablet, a phablet, or any other device capable of communicating via any communication network.

The communication network 114 may include suitable logic, circuitry, interfaces, and/or code, executable by the circuitry, that may be configured to transmit contents and messages between various entities, such as the test-user devices 104, the application server 106, the external database server 108, and/or the target-user device 112. Examples of the communication network 114 may include, but are not limited to, a Wi-Fi network, a light fidelity (Li-Fi) network, a local area network (LAN), a wide area network (WAN), a metropolitan area network (MAN), a satellite network, the Internet, a fiber optic network, a coaxial cable network, an infrared (IR) network, a radio frequency (RF) network, and combinations thereof. Various entities in the environment 100 may connect to the communication network 114 in accordance with various wired and wireless communication protocols, such as Transmission Control Protocol and Internet Protocol (TCP/IP), User Datagram Protocol (UDP), Long Term Evolution (LTE) communication protocols, or any combination thereof.

In operation, the application server 106 may be configured to predict the business outcomes in two phases, such as the learning and prediction phases. The learning phase may focus on generation of the predictor models. During the learning phase, the application server 106 may be configured to retrieve the sample data from the test users 102. The sample data may include the historical data of the test users 102, the images that are of interest to the test users 102, and the answers provided by the test users 102 to the psychometric questions. During the learning phase, the application server 106 may be configured to analyze the sample data for generating the predictor models. For example, the images that are of interest to the test users 102 may be analyzed to extract the feature values for the image features that are object agnostic. The answers provided by the test users 102 may be analyzed to derive the psychometric features, such as personality attributes, of the test users 102. The psychometric features may refer to behavioral qualities or characteristics of an individual's persona. Personality attributes (such as BIG5 attributes and RIASAC Holland occupational themes) are one example of psychometric features. As per BIG5 attributes, the personality attributes may be classified into five areas of: neuroticism, openness, conscientiousness, extraversion, and agreeableness. As per RIASAC Holland occupational themes, the personality attributes may be classified into six categories: Realistic (Doers), Investigative (Thinkers), Artistic (Creators), Social (Helpers), Enterprising (Persuaders), and Conventional (Organizers). Other examples of psychometric features may include, but are not limited to, Gardener's Multiple Intelligences theory related attributes, emotional attributes, aesthetic preferences, and the like. Likewise, the historical data of each test user 102 may be filtered and normalized to remove irrelevant information. The application server 106 may be further configured to utilize the analyzed sample data as input for the machine learning algorithms to generate the predictor models. The analyzed sample data and the predictor models may be stored in the database server 108.

The learning phase may be followed by the prediction phase. During the prediction phase, the application server 106 may be configured to retrieve the target data of the target user 110. The target data may include one or more images that are of interest to the target user 110, identifier links to image interests of the target user 110, answers provided by the target user 110 to the psychometric questions, and/or the historical data of the target user 110. The application server 106 may be further configured to analyze the target data for predicting the business outcomes. For example, the answers provided by the target user 110 may be analyzed to derive the psychometric features, such as personality attributes, of the target user 110 and the images may be analyzed to extract feature values corresponding to the image features. In one embodiment, the application server 106 may be further configured to analyze the historical data of the target user 110 and the images that are of interest to the target user 110 to predict psychometric features of the target user 110. The application server 106 may be further configured to use the derived and predicted psychometric features, the extracted feature values, and/or the analyzed historical data as input to the predictor models for predicting the business outcomes. The learning phase is explained in detail in conjunction with FIG. 3 and the prediction phase is explained in detail in conjunction with FIGS. 4-7.

Figure 2:
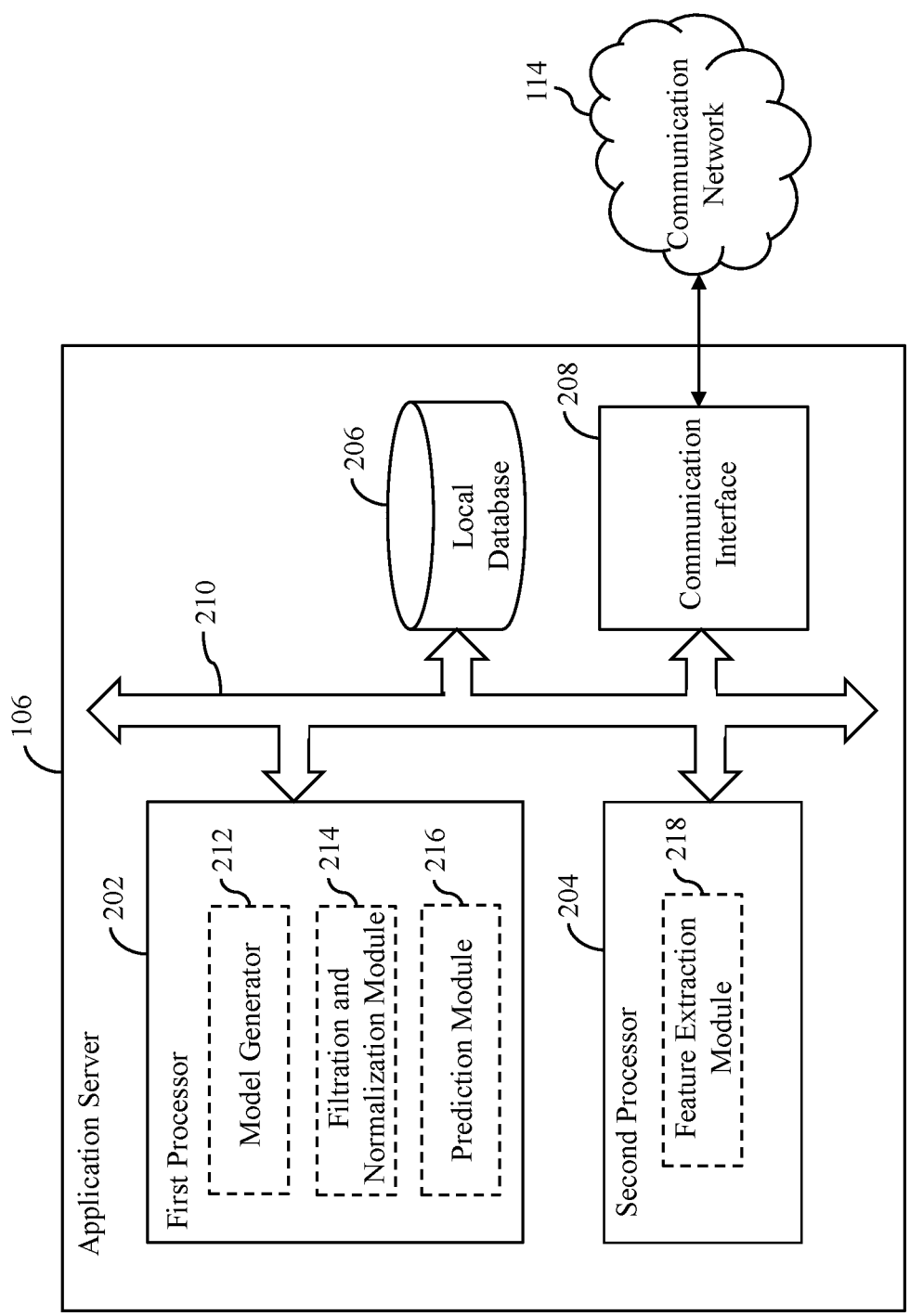
FIG. 2 is a block diagram that illustrates an application server of FIG. 1, in accordance with an embodiment of the disclosure.

FIG. 2 is a block diagram that illustrates the application server 106, in accordance with an embodiment of the disclosure. The application server 106 may include first and second processors 202 and 204, a local database 206, and a communication interface 208. The first and second processors 202 and 204, the local database 206, and the communication interface 208 may communicate with each other by means of a communication bus 210.

The first processor 202 may include suitable logic, circuitry, interfaces, and/or code, executable by the circuitry, that may be configured to perform one or more operations for implementing the learning and prediction phases. The first processor 202 may be configured to obtain the sample data of the test users 102 and the target data of the target user 110. The first processor 202 may be configured to analyze the answers provided by the test users 102 and the target user 110 to the psychometric questions to derive psychometric features for the test users 102 and the target user 110, respectively. Examples of the psychometric features may include, but are not limited to, skills and knowledge, abilities, attitudes, emotional attributes, aesthetic preferences, personality attributes, and/or RIASAC Holland occupational themes. The first processor 202 may include multiple functional blocks, such as: a model generator 212, a filtration and normalization module 214, and a prediction module 216. Examples of the first processor 202 may include, but are not limited to, an application-specific integrated circuit (ASIC) processor, a reduced instruction set computing (RISC) processor, a complex instruction set computing (CISC) processor, a field-programmable gate array (FPGA), and the like.

The second processor 204 may include suitable logic, circuitry, interfaces, and/or code, executable by the circuitry, that may be configured to perform one or more operations for image analysis. The second processor 204 may be an image processor that may include a feature extraction module 218. The feature extraction module 218 may further include suitable logic, circuitry, interfaces, and/or code, executable by the circuitry, that may be configured to extract feature values for various object agnostic image features from the images associated with the test users 102 and the target user 110. The object agnostic image features may include, but are not limited to, color distribution, curves in an image, set of perspective markers in an image, tonality of an image, semantics, or the like. Tonality is the distribution of tones in an image and defines an overall subjective quality of color tones in the image. Tonality includes overall and local contrast in the image, highlight and shadow qualities in the image, and/or the like. Color distribution is a graph that indicates a color level (i.e., number of pixels of each color in the image) in the image as per RGB, CIELUV, or CIELAB color space. Curve in an image is a high-level representation of various shapes present in the image. This representation may be both object agnostic and dependent on a context of representation. The semantics are indicative of contextual meaning conveyed by one or more shapes in the image. For example, two different images may have similar background color, shapes but they may convey different contextual meaning, such as an image of a woman diving under water vs another image of a woman drowning. The object agnostic image features may be independent of one or more objects (such as tags, labels, metadata, or any textual description added to the images) associated with the images. For example, feature values for these object agnostic image features extracted from a first image having a first set of labels may be different from feature values extracted from a second image having the same labels. In one embodiment, the second processor 204 may be configured to use a contextual meaning conveyed by various shapes in the images to extract semantics, curves and shapes from the images. Examples of the second processor 204 may include, but are not limited to, a digital signal processor (DSP), an ASIC processor, a RISC processor, a CISC processor, an FPGA, and the like.

The model generator 212, the filtration and normalization module 214, and the feature extraction module 218 may include suitable logic, circuitry, interfaces, and/or code, executable by the circuitry, that may be configured to implement the learning phase for generating the predictor models. During the learning phase, the sample data may be retrieved and analyzed. For example, the model generator 212 may be configured to analyze the answers provided by the test users 102 for deriving the psychometric features of the test users 102, the filtration and normalization module 214 may be configured to analyze the historical data of the test users 102, and the feature extraction module 218 may be configured to analyze the images associated with the test users 102. The model generator 212 may be configured to use the normalized and filtered historical data, the derived psychometric features, and the extracted feature values for generating the predictor models. For the generation of the predictor models, the model generator 212 may be configured to use various machine learning algorithms such as, but not limited to, regression based predictive learning and neural networks based predictive leaning. In one embodiment, the model generator 212 may be further configured to update the predictor models to improve its prediction accuracy based on a feedback provided by the target user 110 on relevance of the predicted business outcomes.

The filtration and normalization module 214 may be configured to normalize and filter the historical data of the test users 102 and the target user 110. For example, the filtration and normalization module 214 may be configured to filter out the commonly used words (such as "the", "is", "at", "which", "on", and the like) as irrelevant information from the historical data and normalize the remaining historical data to make it more meaningful. In another example, the historical data may be filtered to parse specific keywords. The parsed keywords may include a stream of numbers that represents a mobile number and keywords related to personality, job, likes, dislikes, and the like. The parsed keywords may further correspond to one or more named entities that are related to specific entities (such as: formal or informal names of various institutions, or the like) or actions (such as a sport activity with reference to a place description and a club name) of the test users 102 and the target user 110.

The prediction module 216 may include suitable logic, circuitry, interfaces, and/or code, executable by the circuitry, that may be configured to implement the prediction phase for predicting the business outcomes by using the target data as input to the predictor models. In one embodiment, the prediction module 216 may be configured to use the predictor models to predict psychometric features based on the normalized and filtered historical data and the extracted feature values. The predicted psychometric features may also be used as input for predicting the business outcomes.

The local database 206 may include suitable logic, circuitry, interfaces, and/or code, executable by the circuitry, that may be configured to store the instructions and/or code that enable the first and second processors 202 and 204 to execute their operations. In one embodiment, the local database 206 may be configured to store the sample data, the target data, and the predictor models. Examples of the local database 206 may include, but are not limited to, a random-access memory (RAM), a read-only memory (ROM), a removable storage drive, a hard disk drive (HDD), a flash memory, a solid-state memory, and the like. It will be apparent to a person skilled in the art that the scope of the disclosure is not limited to realizing the local database 206 in the application server 106, as described herein. In another embodiment, the local database 206 may be realized in form of a cloud storage working in conjunction with the application server 106, without departing from the scope of the disclosure.

The communication interface 208 may include suitable logic, circuitry, interfaces, and/or code, executable by the circuitry, that may be configured to transmit and receive data to (or from) various entities, such as the test-user devices 104, the target-user device 112, and/or the external database server 108 over the communication network 114. Examples of the communication interface 208 may include, but are not limited to, an antenna, a radio frequency transceiver, a wireless transceiver, a Bluetooth transceiver, an Ethernet port, a universal serial bus (USB) port, or any other device configured to transmit and receive data. The communication interface 208 may be configured to communicate with the test-user devices 104, the target-user device 112, and the external database server 108 using various wired and wireless communication protocols, such as (TCP/IP), (UDP), LTE communication protocols, or any combination thereof.

Figure 3:
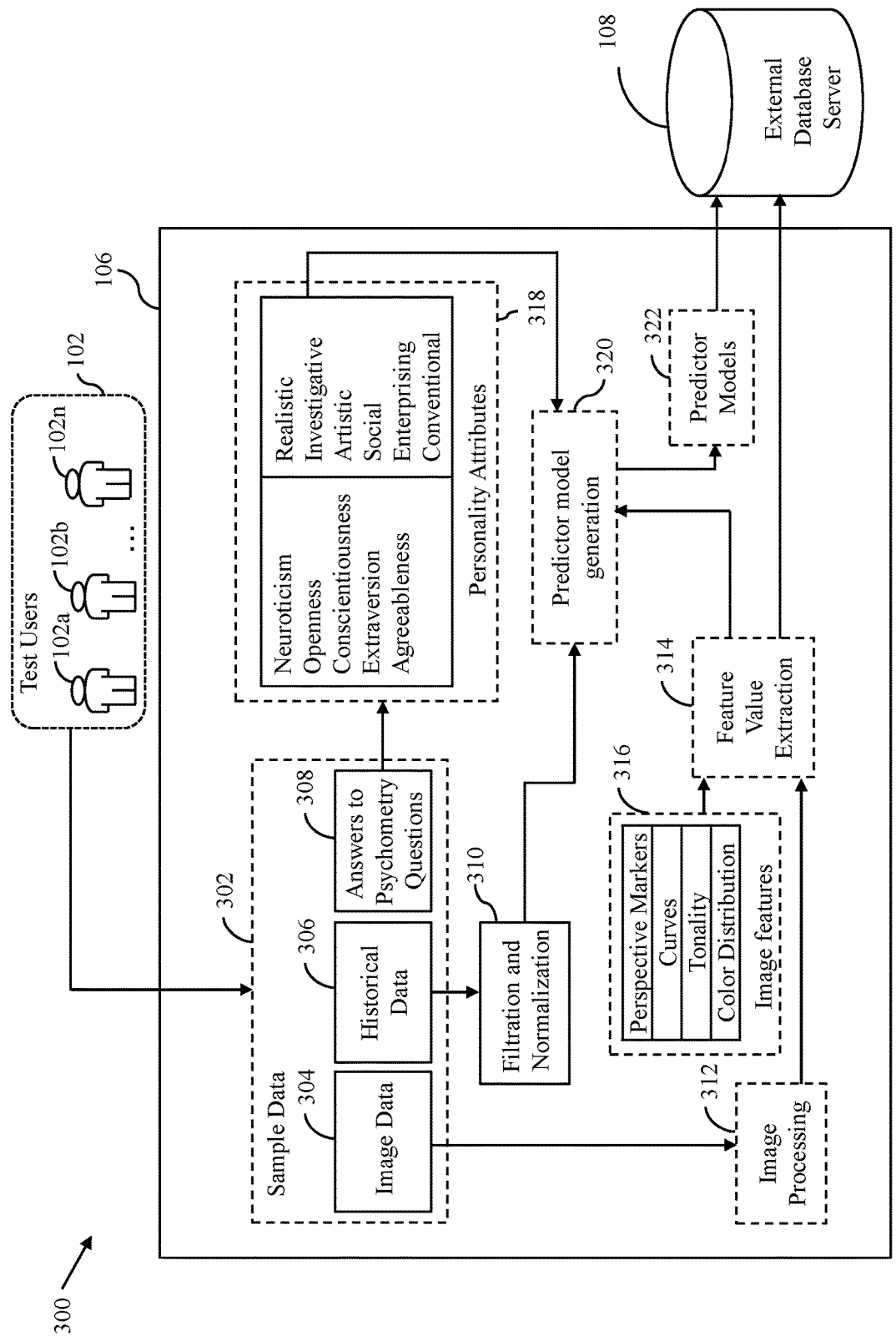
FIG. 3 is a block diagram that illustrates an exemplary scenario for generating predictor models, in accordance with an exemplary embodiment of the disclosure.

FIG. 3 is a block diagram that illustrates an exemplary scenario 300 for generating the predictor models, in accordance with an exemplary embodiment of the disclosure. The exemplary scenario 300 involves the test users 102, the application server 106, and the external database server 108. The application server 106 may be configured to retrieve sample data 302 from the test users 102 as a part of the learning phase. The sample data 302 may include image data 304 associated with the test users 102, historical data 306 of the test users 102, and answers 308 provided by the test users 102 to the psychometric questions. For the sake of simplicity, the retrieval of the sample data 302 is explained with respect to the test user 102a. However, it will be understood by a person of ordinary skill in the art that the application server 106 may be configured to retrieve the sample data 302 of the other test users 102b-102n in a similar manner as described for the test user 102a.

With reference to the test user 102a, the image data 304 may include various images that are of interest to the test user 102a. The application server 106 may be configured to retrieve the images by accessing the activity log of the test user 102a on the internet and the social media platforms based on the consent of the test user 102a. Based on the activity log, the application server 106 may be configured to identify the likes and dislikes of the test user 102a in association with the images. For example, the application server 106 may be configured to utilize an image crawler (not shown) or an image tracker to retrieve the images that the test user 102a views most frequently on the internet and the social media platforms. The application server 106 may be further configured to present multiple images to the test user 102a through the software application that runs on the test-user device 104a and prompt the test user 102a to select images that the test user 102a likes. The images liked by the test user 102a then may be included in the image data 304. The application server 106 may be further configured to utilize the software application that runs on the test-user device 104a to retrieve, with the consent of the test user 102a, images stored in the memory of the test-user device 104a. The image data 304 may further include hyperlinks, web-addresses, uniform resource locators (URLs) of the images that the test user 102a is interested in, and corresponding date and time markers of the images and/or associated links. The date and time markers of an image indicate when the test user 102a has shown interest in the corresponding image or link. The application server 106 may be configured to retrieve the images represented by the hyperlinks, web-addresses, URLs or any other link format that uniquely represents an image and include them in the image data 304. The application server 106 may be further configured to prompt the test user 102a through the test-user device 104a to provide various images that the test user 102a is interested in to the application server 106. The uploaded images may be included in the image data 304.

The historical data 306 of the test user 102a may include, but is not limited to, the curriculum information, the education particulars, the travel history, the employment details, the purchase history of the test user 102a, and one or more posts that are shared, followed, and liked by the test user 102a on the internet and the social media platform. For example, the test-user device 104a, executing the software application, may be configured to access the activity log of the test user 102a on the internet to obtain the travel history and the purchase history of the test user 102a. Based on a consent of the test user 102a, the test-user device 104a may be further configured to access the social media profile (for example LinkedIn®, Facebook®, or the like) of the test user 102a to obtain education and job particulars of the test user 102a, and one or more posts that are shared, followed, and liked by the test user 102a on the social media profile. The application server 106 may be further configured to communicate a questionnaire to the test-user device 104a regarding the historical data of the test user 102a. The test-user device 104a may be configured to communicate to the application server 106 a response provided by the test user 102a to the questionnaire and the application server 106 may be configured to the include the response of the test user 102a in the historical data 306.

The application server 106 may be configured to prompt the test user 102a to take one or more online or offline tests (such as, but not limited to, the multiple intelligence quiz, the BIG 5, or the personal globe inventory) including the psychometric questions. The test user 102a may provide the answers 308 to the psychometric questions. The answers 308 to the psychometric questions are then provided by the test user 102a and communicated to the application server 106 by the test-user device 104a. In one exemplary scenario, the psychometric questions may include one hundred questions each of which is associated with a linear scale. For example, the linear scale may be scored from 0 to 9, where score '0' means there is no correlation between the test user 102a and a question statement and score '9' means the test user 102a and the question statement completely corelate. In this scenario, the answer 308 to each psychometric question may be a score selected by the test user 102a from the linear scale. In another exemplary scenario, the psychometric questions may include one hundred questions each of which is associated with a set of options, such as four options, having a specific score associated thereto. The test user 102a may be required to select one or more options from the set of options for each psychometric question as the answer 308. It will be apparent to a person of skill in the art that the abovementioned examples are for illustrative purpose and should not be construed to limit the scope of the disclosure.

In another embodiment, the application server 106 may be further configured to retrieve the answers 308 from third-party servers (not shown) that conduct psychometric analysis of various users via online or offline tests.

After retrieving the sample data 302 of the test users 102, the application server 106 may be configured to process the sample data 302. Processing of the sample data 302 may involve filtering and normalizing the historical data 306 (as represented by block 310). For example, the historical data 306 retrieved from the test users 102 may include irrelevant information. Thus, the filtration and normalization module 214 may be configured to filter out and normalize the historical data 306 so that only relevant information is processed further. For example, the filtration and normalization module 214 may be configured to filter the commonly used words (such as "the", "is", "at", "which", "on", and the like) as irrelevant information from the historical data 306 and normalize the remaining historical data 306 to make it more meaningful. In another example, the filtration and normalization module 214 may be configured to parse specific keywords, such as, but not limited to, identifying a stream of numbers that may represent a mobile number, extracting keywords related to personality, job, likes, dislikes, or the like, in the historical data 306. In another example, the filtration and normalization module 214 may be configured to extract one or more named entities which are related to specific objects or actions (for example, identifying full name of an institution by recognizing informal name of the institution in a post) from the historical data 306 and recognize one or more activities which are mentioned indirectly (for example, recognizing a type of sport activity by referring a place description or a club name in a post) in the historical data 306.

Processing of the sample data 302 may further involve analyzing the image data 304. For analyzing each image in the image data 304, the feature extraction module 218 may be configured to perform image processing (as represented by block 312) followed by feature value extraction (represented by block 314). Before analyzing the image data 304, the feature extraction module 218 may be configured to query the external database server 108 to identify images from the image data 304 that are already analyzed by the feature extraction module 218 during previous learning and prediction phases. The feature extraction module 218 may not analyze the already analyzed images for feature extraction and may query the external database server 108 to retrieve the feature values corresponding to the already analyzed images. In one scenario, the application server 106 may be configured to use the date and time markers of the images and/or the associated links for image processing and feature value extraction. In other words, the application server 106 may be configured to perform image processing and feature value extraction in a chronological order based on the date and time markers. For example, the application server 106 may be configured to process an image for which the test user 102a has shown interest one month ago before an image for which the test user 102a has shown interest one day ago. The image processing may involve resampling an image for magnification or minification (i.e., to modify a color scale associated with an image), removing duplicate copies of an image in the image data 304, pre-processing the image to convert it to a pixelated image (if required), denoising the image, and attaining a predefined resolution format (e.g. 128×128, 256×256, 1024×768 and the like).

During feature value extraction, the feature extraction module 218 may be configured to extract feature values from the images included in the image data 304 corresponding to image features (as represented by block 316) that are object agnostic (i.e., independent of the objects associated with the image). The image features may include, but are not limited to, color distribution, curves, perspective markers, and tonality. For example, extracting color distribution for a set of colors present in an image of the image data 304 may include resampling the image and modification of a color space associated with the original image (i.e., the non-resampled image). As different color spaces, such as RGB, sRGB, CIELAB, and/or CIEXYZ, define different color scales (i.e., spatial and tonal resolutions), the feature extraction module 218 may be configured to normalize the colors present in the image to a particular color space having tone comparable scales, before extracting the color distribution from the image. In one scenario, a color scale of the re-sampled image may include multiple colors. In this scenario, the feature extraction module 218 may be configured to group a sub-set of colors and extract color distribution for the group of colors or individual colors associated with the group. In one embodiment, the feature extraction module 218 may be configured to determine a dominant color of the group of colors based on one or more parameters (e.g., number of pixels of the corresponding color in the image). In another scenario, the color scale of the re-sampled image may not include multiple colors. In this scenario, the feature extraction module 218 may be configured to extract distribution of a color that is nearest to the color present in the color space of the resampled image. Likewise, the feature extraction module 218 may be configured to extract feature values for other image features 316. It will be understood by a person of ordinary skill in the art that the block 316 is shown for illustrative purposes and should not be construed to limit the scope of the disclosure. Thus, the image features may include any image feature that is object agnostic without deviating from the scope of the disclosure. In one embodiment, the feature extraction module 218 may be configured to combine the extracted feature values corresponding to the images of the image data 304. For example, the feature extraction module 218 may normalize and adjust the extracted feature values corresponding to the images of each test user 102 to obtain a specific set of feature values for each test user 102. The feature extraction module 218 may be further configured to store the extracted feature values corresponding to each image in the external database server 108.

Processing of the sample data 302 may further involve analyzing the answers 308 to derive psychometric features of the test users 102. For the sake of ongoing description, the psychometric features are assumed to include, but are not limited to, personality attributes such as neuroticism, openness, conscientiousness, extraversion, agreeableness, realistic, investigative, artistic, social, enterprising, and conventional (as represented by block 318). It will be understood by a person of ordinary skill in the art that the block 318 is shown for illustrative purposes and should not be construed to limit the scope of the disclosure. Thus, the derived psychometric features may include other psychometric features as well without deviating from the scope of the disclosure. The first processor 202 may be configured to analyze the answers 308 corresponding to each test user 102 for deriving psychometric features of the test user 102a. In an exemplary scenario, each of the psychometric feature in the block 318 may be associated with a corresponding range of a psychometric score. For example, neuroticism may be associated with the range [42,60] for the psychometric score that varies between [0,100]. When the psychometric score has the value between 42-60, neuroticism has a confidence score of '1'. The confidence score of neuroticism may decrease as the psychometric score deviates from the corresponding range. Likewise, the other psychometric features may be associated with the corresponding range of the psychometric score. When the first processor 202 receives the answers 308, the first processor 202 may be configured to determine the psychometric score for the test user 102a. In one example, when the answers 308 provided by the test user 102a include a score selected by the test user 102a from the linear scale associated with each psychometric question, the psychometric score may be equal to a cumulative sum of the scores selected by the test user 102a. In another example, when the answers 308 provided by the test user 102a include one or more options selected by the test user 102a from the set of options associated with each psychometric question, the psychometric score may be equal to a cumulative sum of the scores associated with the options selected by the test user 102a. For deriving the psychometric features of the test user 102a, the first processor 202 may be configured to determine the confidence score for each psychometric feature in the block 318 based on the determined psychometric score of the test user 102a. It will be apparent to a person of skill in the art that the abovementioned exemplary scenario is for illustrative purpose and should not be construed to limit the scope of the disclosure. The first processor 202 may derive the psychometric features in the block 318 from the answers 308 by using by any technique known in the art.

After the sample data 302 is processed, the model generator 212 may be configured to use the analyzed historical data 306, the combined feature values extracted from the image data 304, and the derived psychometric features as inputs for predictor model generation (as represented by block 320). The model generator 212 may be configured to use one or more machine learning algorithms, such as regression based predictive learning, neural networks based predictive leaning, and the like, for generating various predictor models (such as predictor models 322). During the generation of the predictor models 322, the model generator 212 may be configured to map the image features and the analyzed historical data 306 with the psychometric features based on the extracted feature values and generate links therebetween. In other words, a linear combination of image features is linked to each psychometric feature based on the extracted feature values. For example, in a linear regression model, for a first set of feature values extracted from the images that are of interest to the test user 102a, the image features may be mapped to the confidence scores of each of the psychometric features derived for the test user 102a. For a second set of feature values extracted from the images that are of interest to the test user 102b, the image features may be mapped to the confidence scores of each of the psychometric features derived for the test user 102b. Likewise, the analyzed historical data may be mapped with the psychometric features. The model generator 212 may be configured to assign weights to the generated links. The assigned weights indicate the strength of association between the specific image feature and the derived psychometric features. For example, the model generator 212 may assign a first set of weights to a first set of links between the image features and the psychometric features derived for the test user 102a. In one scenario, when the second set of feature values extracted from the images that are of interest to the test user 102b are same as the first set of feature values and the confidence scores of the psychometric features derived for the test user 102b are same as of the user 102a, the model generator 212 may be configured to increase the first set of weights assigned to the first set of links. However, if the second set of feature values are different from the first set of feature values and/or the confidence scores of the psychometric features derived for the test user 102b are not same as of the user 102a, the model generator 212 may be configured to adjust the first set of weights assigned to the first set of links and may generate a second set of links having a second set of weights between the image features and the psychometric features derived for the test user 102b. Similarly, the model generator 212 may assign weights to the links generated between the image features and the psychometric features derived for other test users 102c-102n. The model generator 212 may be configured to generate the predictor models 322 by using the weighted links. It will be apparent to a person of ordinary skill in the art that the abovementioned examples are for illustrative purpose, the model generator 212 may use other complex models of mapping the image features to the psychometric features without deviating from the scope of the disclosure.

The predictor models 322 generated by the model generator 212 may include at least three predictor models 322. The first predictor model may be capable of predicting psychometric features by using feature values extracted from an image as input. For example, the first predictor model may be capable of predicting psychometric features based on the color distribution of all the colors present in the images that are of interest to the target user 110 regardless of color grouping during the analysis of the images. In another example, the first predictor model may be capable of predicting the psychometric features of the target user 110 based on distribution of the group of colors (as represented by Kobayashi color distribution, or the like) in the images. In another example, the first predictor model may be capable of predicting the psychometric features of the target user 110 based on distribution a single dominant color in the images. In another example, the first predictor model may be capable of predicting the psychometric features of the target user 110 based on curve-based features, perspective markers, and/or semantics presented as multidimensional vectors.

The second predictor model may be capable of predicting psychometric features by using analyzed historical data 306 as input. The third predictor model may capable of predicting business outcomes by using predicted and derived psychometric features and feature values extracted from one or more images as input. The model generator 212 may be configured to store the three predictor models 322 in the external database server 108. The predictor models 322 may be used by the prediction module 216 for predicting business outcomes, as described in conjunction with FIGS. 4-7.

Figure 4:
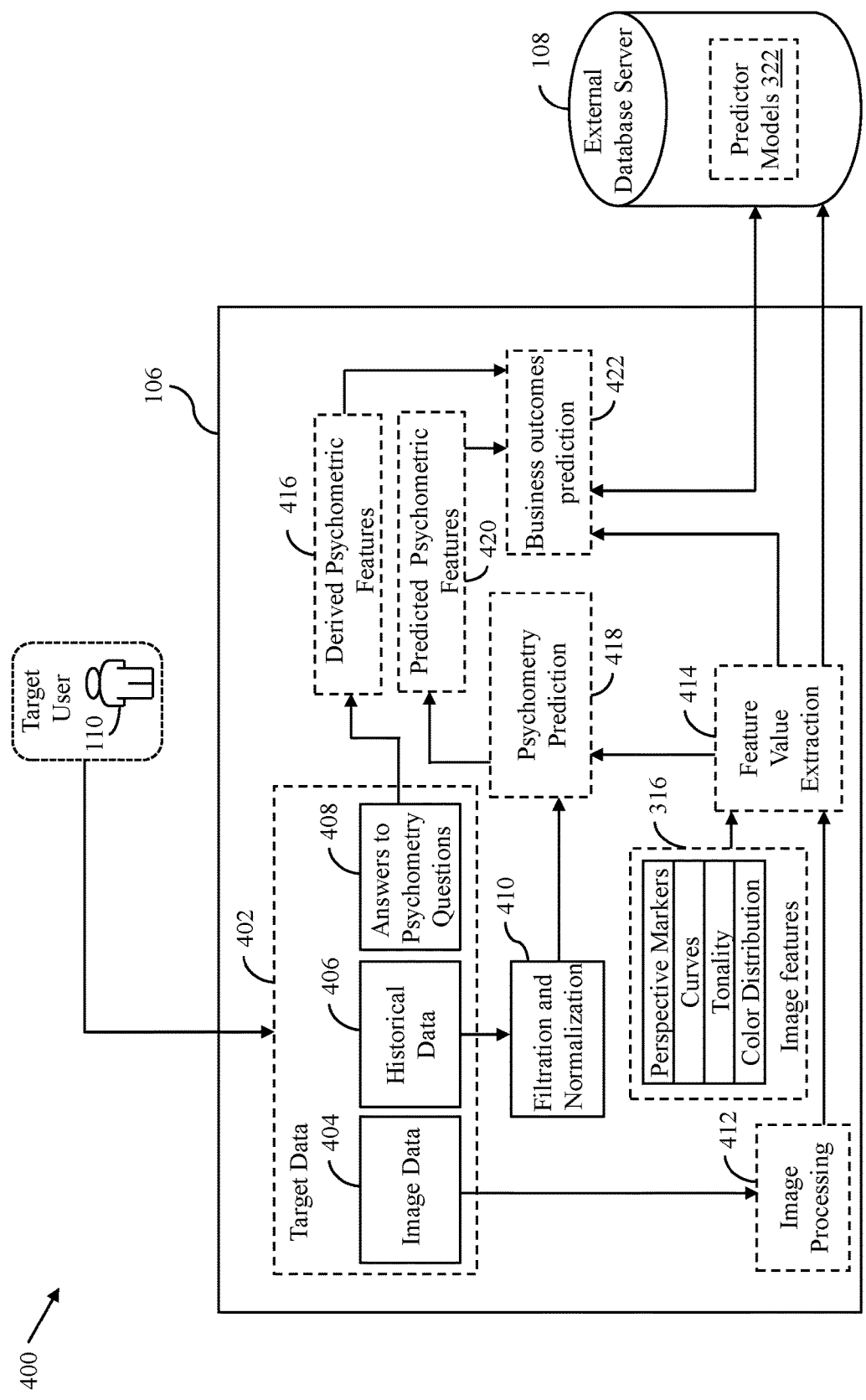
FIG. 4 is a block diagram that illustrates an exemplary scenario for predicting business outcomes, in accordance with an exemplary embodiment of the disclosure.

FIG. 4 is a block diagram that illustrates an exemplary scenario 400 for predicting business outcomes, in accordance with an exemplary embodiment of the disclosure. The exemplary scenario 400 involves the target user 110 who may provide target data 402, the application server 106, and the external database server 108 that may store the predictor models 322. The exemplary scenario 400 illustrates a scenario where the target data 402 may include image data 404 of the target user 110, historical data 406 of the target user 110, and answers 408 provided by the target user 110 to the psychometric questions.

The image data 404 may include various images that are of interest to the target user 110. The application server 106 may be configured to retrieve the images by accessing an activity log of the target user 110 on the internet and the social media platforms based on a consent of the target user 110. Based on the activity log, the application server 106 may be configured to identify the likes and dislikes of the target user 110 in association with the images. For example, the application server 106 may be configured to utilize the image crawler to retrieve the images that the target user 110 views most frequently on the internet and the social media platforms. The application server 106 may be further configured to present multiple images to the target user 110 through the software application that runs on the target-user device 112 and prompt the target user 110 to select images that the target user 110 likes. The images liked by the target user 110 are may be included in the image data 404. The application server 106 may be configured to utilize the software application running on the target-user device 112 for retrieving, with the consent of the target user 110, images stored in the memory of the target-user device 112. The image data 404 may further include hyperlinks, web-addresses, URLs of the images that the target user 110 is interested in, and corresponding date and time markers of images and/or associated links. The application server 106 may be configured to retrieve the images represented by the hyperlinks, web-addresses, and URLs and include them in the image data 404. The application server 106 may be further configured to prompt the target user 110 by way of the software application to upload various images that the target user 110 may be interested in. The uploaded images may be included in the image data 404.

The historical data 406 of the target user 110 may include, but is not limited to, the curriculum information, the education particulars, the travel history, the employment details, and/or the purchase history of the target user 110. For example, the target-user device 112 may be configured to access the activity log of the target user 110 on the internet for providing the travel history and the purchase history of the target user 110 to the application server 106. Based on a consent of the target user 110, the application server 106 may be configured to utilize the software application that runs on the target-user device 112 for accessing the social media profile (for example LinkedIn®, Facebook®, and the like) of the target user 110 and retrieving the education and job particulars of the target user 110, and one or more posts that are shared, liked, or followed by the target user 110 on the social media profile. In one embodiment, the application server 106 may be configured to prompt the target user 110 by way of the target-user device 112 to provide additional historical data. The application server 106 may be further configured to communicate a questionnaire to the target user 110 regarding the historical data 406 of the target user 110 through the target-user device 112. The target-user device 112 may be configured to communicate to the application server 106 a response provided by the target user 110 to the questionnaire and the application server 106 may be configured to the include the response of the target user 110 in the historical data 406.

The application server 106 may be configured to prompt the target user 110 to take one or more online or offline tests (such as, but not limited to, the multiple intelligence quiz, the BIG 5, or the personal globe inventory) including the psychometric questions. The target user 110 may provide the answers 408 to the psychometric questions. In another embodiment, the application server 106 may be further configured to retrieve the answers 408 from the third-party servers that conduct the psychometry analysis of users via online or offline tests. The answers 408 may be similar to the answers 308.

After retrieving the target data 402, the application server 106 may be configured to process the target data 402. Processing of the target data 402 may involve filtering and normalizing the historical data 406 (as represented by block 410). Processing of the target data 402 may further involve analyzing the image data 404. Before analyzing the image data 404, the feature extraction module 218 may query the external database server 108 to identify images in the image data 404 and/or images corresponding to the URLs (or any other link format that uniquely represents an image) included the image data 404 that are already analyzed by the feature extraction module 218 during the learning phase. The feature extraction module 218 may not analyze the already analyzed images for feature extraction and may query the external database server 108 to retrieve the feature values corresponding to the already analyzed images. For analyzing the images in the image data 404 that have not been analyzed during the learning phase, the feature extraction module 218 may perform image processing (as represented by block 412) followed by feature value extraction (as represented by block 414). The first processor 202 may be further configured to retrieve images corresponding to the URLs included in the image data 404 and the second processor 204 may be configured to perform image processing and feature value extraction on the retrieved images if they are not analyzed previously. In one scenario, the application server 106 may be configured to use the date and time markers of the images and/or the associated links, for image processing and feature value extraction. For example, the application server 106 may process an image for which the target user 110 has shown interest one month ago before an image for which the target user 110 has shown interest one day ago. During feature value extraction, the feature extraction module 218 may be configured to extract the feature values corresponding to the image features (as represented by block 316). The image features may include, but are not limited to, color distribution, curves, perspective markers, and/or tonality. In one embodiment, the extracted feature values may correspond to a multidimension vector.

In an exemplary scenario, extracting color distribution for a set of colors present in an image of the image data 404 may include resampling the image to modify a color space associated with the original image (i.e., the non-resampled image). As different color spaces, such as RGB, sRGB, CIELAB, and/or CIEXYZ, define different color scales (i.e., spatial and tonal resolutions), the feature extraction module 218 may be configured to normalize the colors present in the image to a particular color space having tone comparable scales, before extracting the color distribution from the image. In one scenario, a color scale of the re-sampled image may include multiple colors. In this scenario, the feature extraction module 218 may be configured to group a sub-set of colors and extract color distribution for the group of colors or individual colors associated with the group. In one embodiment, the feature extraction module 218 may be configured to determine a dominant color of the group of colors based on one or more parameters (e.g., number of pixels of the corresponding color in the image). In another scenario, the color scale of the re-sampled image may not include multiple colors. In this scenario, the feature extraction module 218 may be configured to extract distribution of a color that is nearest to the color present in the color space of the resampled image. Likewise, the feature extraction module 218 may be configured to extract feature values for other image features 316. In one embodiment, the feature extraction module 218 may normalize and adjust the extracted feature values corresponding to the images of the target user 110 to obtain a combined set of feature values for the target user 110.

The feature extraction module 218 may be configured to store the extracted feature values corresponding to each image in the external database server 108. Processing of the target data 402 may further involve analyzing the answers 408 by the first processor 202 for deriving psychometric features 416 (hereinafter designated and referred to as "derived psychometric features 416") of the target user 110.

After the target data 402 is processed, the prediction module 216 may be configured to query the external database server 108 to retrieve the predictor models 322. The prediction module 216 may be further configured to use the feature values extracted from the image data 404 and the analyzed historical data 406 as input to the first and second predictor models, respectively, for psychometry prediction (as represented by block 418). The psychometry prediction may yield predicted psychometric features 420 of the target user 110 as output. In one embodiment, the prediction module 216 may be configured to predict psychometric features separately for each image of the image data 404 by using the first predictor model. After the psychometric features are predicted for each image of the image data 404, the prediction module 216 may be configured to normalize and adjust the psychometric features to yield the predicted psychometric features 420. In another embodiment, the prediction module 216 may be configured to normalize and combine the feature values extracted from the images of the image data 404 and use the normalized and combined feature values as input to the first predictor model for obtaining the predicted psychometric features 420.

The prediction module 216 may be configured to use the combined feature values extracted from the image data 404, the derived psychometric features 416, and the predicted psychometric features 420 as input to the third predictor model for predicting business outcomes (as represented by block 422). The application server 106 may be configured to store the predicted business outcomes in the external database server 108. In an embodiment, the business outcomes may include, but are not limited to, job suggestions, purchase suggestions, targeted advertisements, image suggestions, compatibility match, and the like. Due to chronological processing of the image data 404 based on the date and time markers, the application server 106 may be capable of predicting the business outcomes as per behavioral changes exhibited by the target user 110 over a period of time. The application server 106 may be configured to communicate the predicted business outcomes to the target user 110.

Thus, based on the predicted business outcomes, intelligent and informed decisions (such as accepting or denying a job offer, purchasing a new product, listening suggested music files, and the like) may be made by the target user 110. In another embodiment, the business outcomes may include, but are not limited to, purchase trend of various commodities, affinity of the target user 110 for one or more activities, and the like. The application server 106 may communicate the predicted business outcomes to an organization, such as a social media provider, an e-commerce provider, or the like. Thus, based on the predicted business outcomes, intelligent and informed decisions (such as providing relevant job suggestions to the target user 110 on the social media profile of the target user 110 or customizing the social media profile of the target user 110 based on the interests of the target user 110) may be made by the social media provider. Likewise, based on the predicted business outcomes, an e-commerce platform may make intelligent decisions, such as updating their inventory based on the purchase trend. The e-commerce platform may divide customers into different groups based on their common purchase interests (i.e., business outcomes). Moreover, deep personalization of a customer (i.e., analyzing image interests of the customer) to understand more complex patterns of customer behavior (i.e., business outcomes) and preferences may help the e-commerce platform to grow. Similarly, an educational institute, such as a university, may use the predicted business outcomes to offer admission to various students or understand requirement of new equipment, stationery to be installed.

In another exemplary scenario, the target user 110 may be a person to be hired by an organization. In this scenario, the organization may obtain and analyze image samples, that are of interest to the target user 110, by using the predictor models 322 to get accurate prediction of personality of the target user 110, without asking any question to the target user. In another exemplary scenario, the target user 110 may be an employee of the organization, whose employment affinity (i.e., a business outcome) is of interest to the organization, such as for employee retention and engagement.

It will be understood by a person of ordinary skill in the art that the abovementioned business outcomes are listed for exemplary purpose and should not be construed to limit the scope of the disclosure. In other embodiments, the predictor models 322 may be utilized to predict business outcomes that are different from the business outcomes mentioned above.

In one embodiment, the application server 106 may be configured to render a user interface (UI) on the target-user device 112 for presenting the predicted business outcomes to the target user 110. In one example, the application server 106 may be configured to render the UI through the software application that runs on the target-user device 112. A feedback (for example, a common score or an individual score for each business outcome) may be provided by the target user 110 to indicate a relevance of the predicted business outcomes. For example, when the business outcomes have high relevance to the target user 110, the target user 110 may provide a positive feedback. In another example, when the business outcomes have low relevance to the target user 110, the target user 110 may provide a negative feedback. The model generator 212 may be configured to use the feedback provided by the target user 110 to update the predictor models 322 for improving their accuracy. The model generator 212 may be further configured to adjust the weight of links between the image features and the psychometric features (e.g., the personality attributes) based on the feedback.

Figure 5:
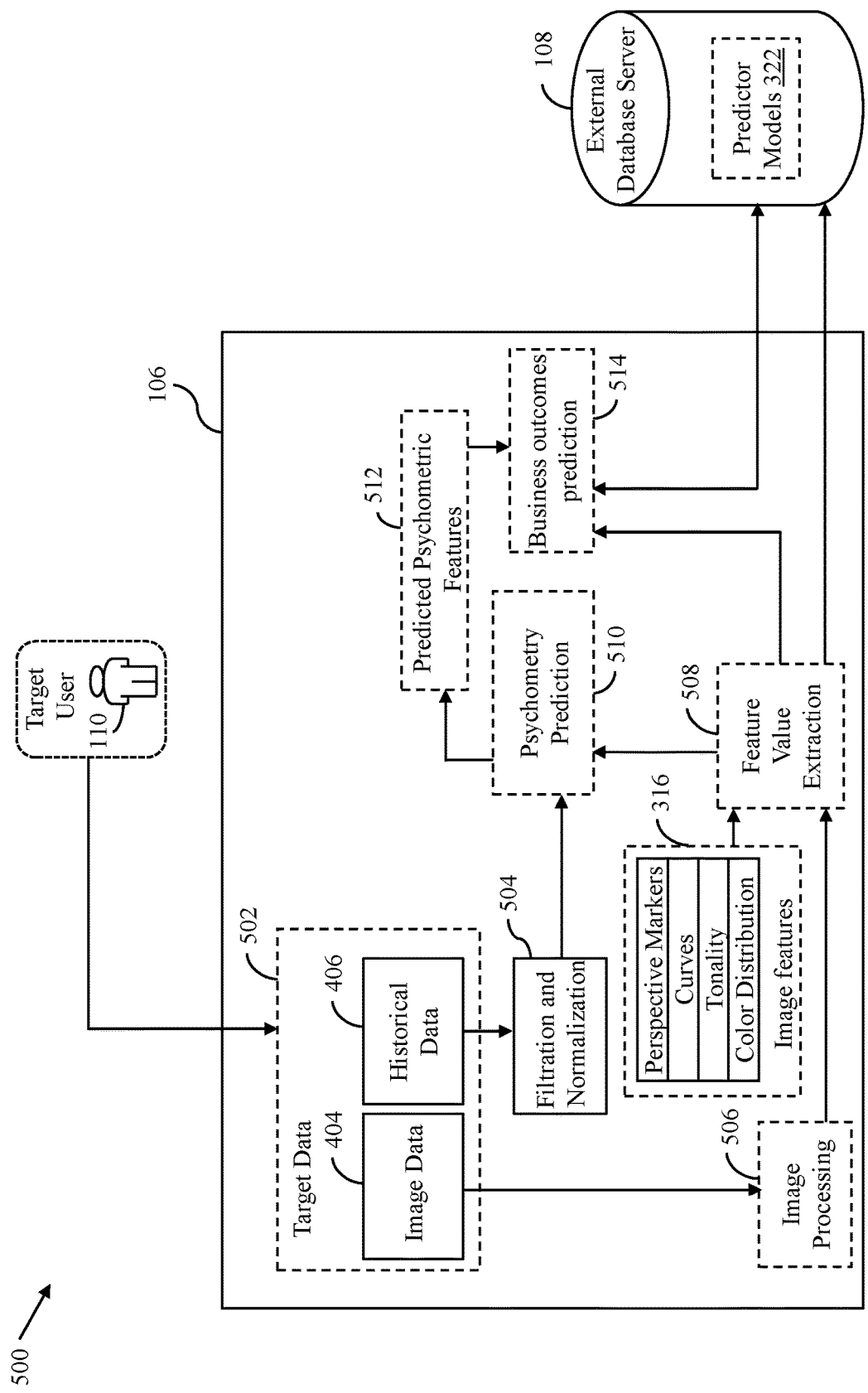
FIG. 5 is a block diagram that illustrates another exemplary scenario for predicting business outcomes, in accordance with another exemplary embodiment of the disclosure.

FIG. 5 is a block diagram that illustrates another exemplary scenario 500 for predicting business outcomes, in accordance with another exemplary embodiment of the disclosure. The exemplary scenario 500 involves the target user 110 who may provide target data 502, the application server 106, and the external database server 108 that may store the predictor models 322. The exemplary scenario 500 illustrates a scenario where the target data 502 may include the image data 404 of the target user 110 and the historical data 406 of the target user 110. The application server 106 may be configured to retrieve the target data 502 in a manner similar to the retrieval of the target data 402 as explained in FIG. 4.

After retrieving the target data 502, the application server 106 may be configured to process the target data 502. The filtration and normalization module 214 may be configured to filter and normalize the historical data 406 (as represented by block 504). Before analyzing the image data 404, the feature extraction module 218 may be configured to query the external database server 108 to identify images in the image data 404 and/or images corresponding to the URLs (or any other link format that uniquely represents an image) included the image data 404 that are already analyzed by the feature extraction module 218 during previous learning or prediction phases. The feature extraction module 218 may not analyze the already analyzed images for feature extraction and may query the external database server 108 to retrieve the feature values corresponding to the already analyzed images. The feature extraction module 218 may be configured to perform image processing (as represented by block 506) followed by feature value extraction (as represented by block 508) on the images that are not analyzed yet. During feature value extraction, the feature extraction module 218 may be configured to extract the feature values corresponding to the image features (as represented by block 316). The feature extraction module 218 may be further configured to store the extracted feature values corresponding to each image in the external database server 108. Since the target data 502 may not include the answers 408 to the psychometric questions, the first processor 202 may not be configured to derive any psychometric features of the target user 110 based on the answers 408.

After the target data 502 is processed, the prediction module 216 may be configured to query the external database server 108 to retrieve the predictor models 322. The prediction module 216 may be further configured to use the feature values extracted from the image data 404 and the analyzed historical data 406 as input to the first and second predictor models, respectively, for psychometry prediction (as represented by block 510). The psychometry prediction may yield predicted psychometric features 512 as output.

The prediction module 216 may be configured to use the feature values extracted from the image data 404 and the predicted psychometric features 512 as input to the third predictor model for predicting the business outcomes (as represented by block 514). The predicted business outcomes may be relevant to the target user 110 and/or an organization as described in FIG. 4. The application server 106 may be configured to store the predicted business outcomes in the external database server 108.

Figure 6:
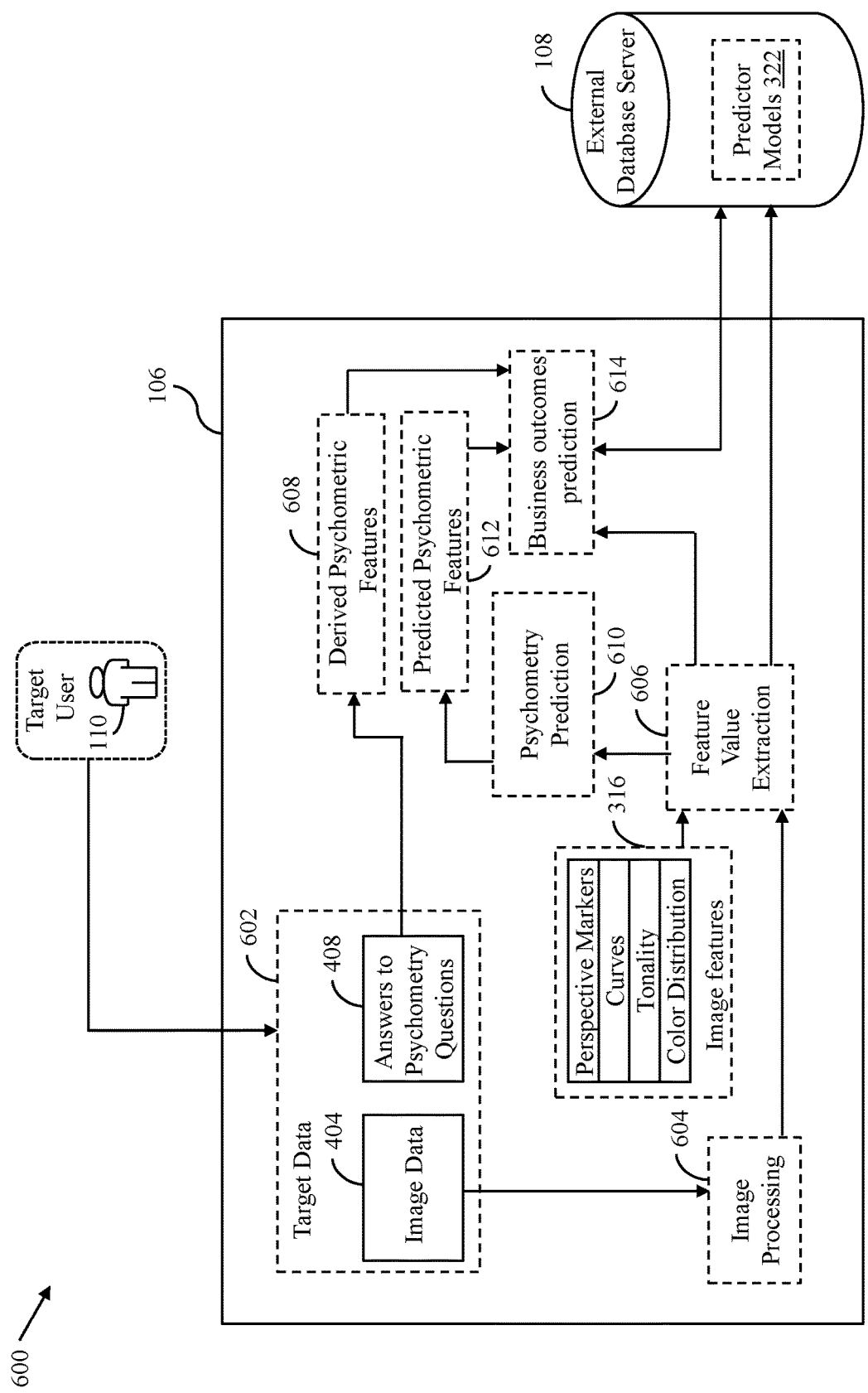
FIG. 6 is a block diagram that illustrates another exemplary scenario for predicting business outcomes, in accordance with another exemplary embodiment of the disclosure.

FIG. 6 is a block diagram that illustrates an exemplary scenario 600 for predicting business outcomes, in accordance with another exemplary embodiment of the disclosure. The exemplary scenario 600 involves the target user 110 who may provide target data 602, the application server 106, and the external database server 108 that may store the predictor models 322. The exemplary scenario 600 illustrates a scenario where the target data 602 may include the image data 404 of the target user 110 and the answers 408 provided by the target user 110 to the psychometric questions. The application server 106 may be configured to retrieve the target data 602 in a manner similar to the retrieval of the target data 402 as explained in FIG. 4.

After retrieving the target data 602, the application server 106 may be configured to process the target data 602. Before analyzing the image data 404, the feature extraction module 218 may be configured to query the external database server 108 to identify images in the image data 404 and/or images corresponding to the URLs (or any other link format that uniquely represents an image) included the image data 404 that are already analyzed by the feature extraction module 218 during the previous learning or prediction phases. The feature extraction module 218 may not analyze the already analyzed images for feature extraction and may query the external database server 108 to retrieve the feature values corresponding to the already analyzed images. The feature extraction module 218 may be configured to perform image processing (as represented by block 604) followed by feature value extraction (as represented by block 606) on the images that are not analyzed yet. During feature value extraction, the feature extraction module 218 may be configured to extract the feature values corresponding to the image features (as represented by block 316). The feature extraction module 218 may be further configured to store the extracted feature values corresponding to each image in the external database server 108. Processing of the target data 602 may further involve analyzing the answers 408 by the first processor 202 for deriving psychometric features 608 (hereinafter designated and referred to as "derived psychometric features 608") of the target user 110.

After the target data 602 is processed, the prediction module 216 may be configured to query the external database server 108 to retrieve the predictor models 322. The prediction module 216 may be further configured to use the feature values extracted from the image data 404 as input to the first predictor model for psychometry prediction (as represented by block 610). The psychometry prediction may yield predicted psychometric features 612 as output.

The prediction module 216 may be configured to use the feature values extracted from the image data 404, the derived psychometric features 608, and the predicted psychometric features 612 as input to the third predictor model for predicting the business outcomes (as represented by block 614). The predicted business outcomes may be relevant to the target user 110 and/or an organization as described in FIG. 4. The application server 106 may be configured to store the predicted business outcomes in the external database server 108.

Figure 7:
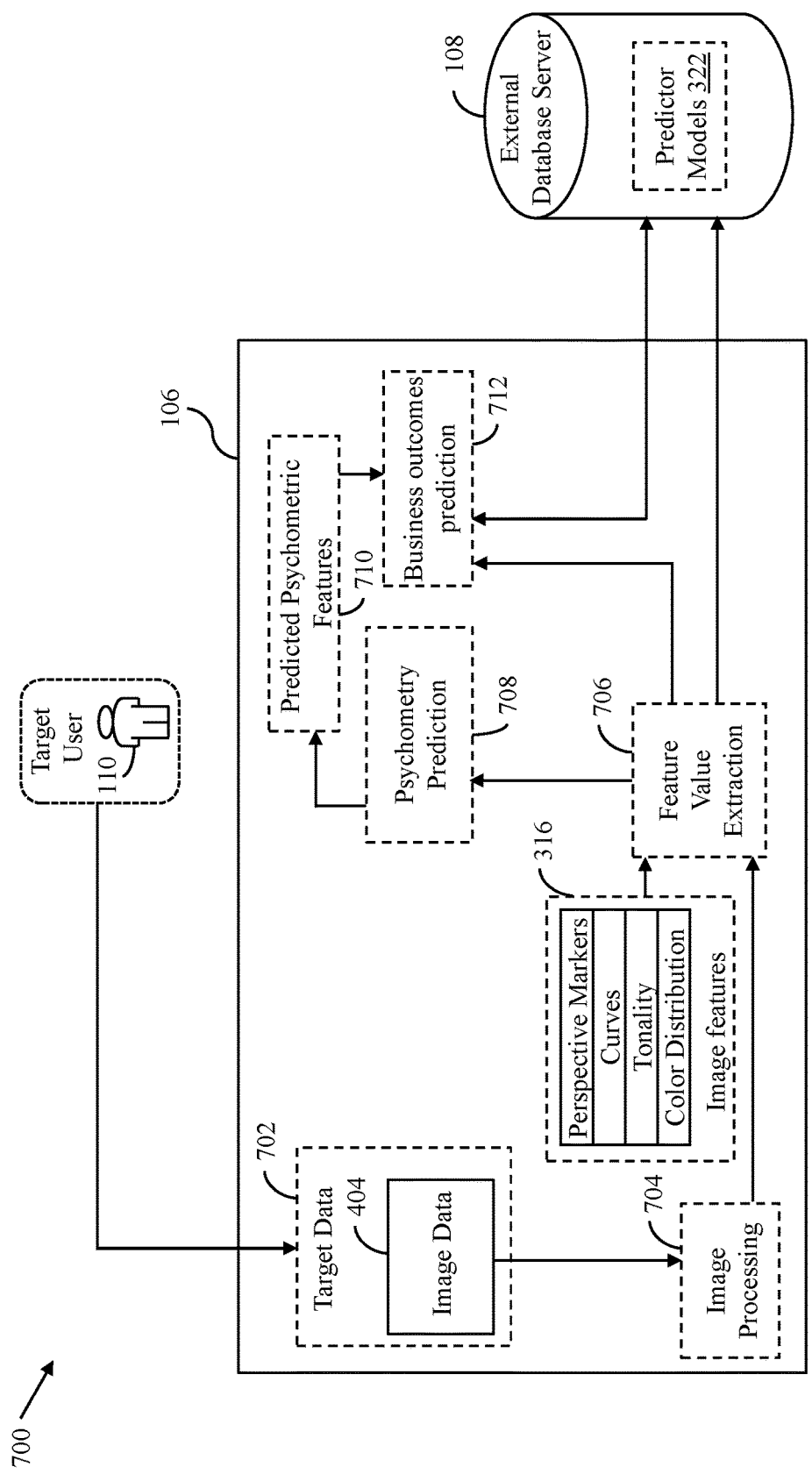
FIG. 7 is a block diagram that illustrates another exemplary scenario for predicting business outcomes, in accordance with another exemplary embodiment of the disclosure.

FIG. 7 is a block diagram that illustrates an exemplary scenario 700 for predicting business outcomes, in accordance with another exemplary embodiment of the disclosure. The exemplary scenario 700 involves the target user 110 who may provide target data 702, the application server 106, and the external database server 108 that may store the predictor models 322. The exemplary scenario 700 illustrates a scenario where the target data 702 may include only the image data 404 of the target user 110. The application server 106 may be configured to retrieve the target data 702 in a manner similar to the retrieval of the target data 402 as explained in FIG. 4.

After retrieving the target data 702, the application server 106 may be configured to process the target data 702. Before analyzing the image data 404, the feature extraction module 218 may be configured to query the external database server 108 to identify images in the image data 404 and/or images corresponding to the URLs (or any other link format that uniquely represents an image) included the image data 404 that are already analyzed by the feature extraction module 218 during the previous learning and prediction phases. The feature extraction module 218 may be configured to perform image processing (as represented by block 704) followed by feature value extraction (as represented by block 706) on the images in the image data 404 that are not analyzed yet. During feature value extraction, the feature extraction module 218 may be configured to extract the feature values corresponding to the image features (as represented by block 316). The feature extraction module 218 may be further configured to store the extracted feature values corresponding to each image in the external database server 108. Since the target data 702 may not include the answers 408 to the psychometric questions, the first processor 202 may not derive any psychometric features of the target user 110 based on the answers 408.

After the target data 702 is processed, the prediction module 216 may be configured to query the external database server 108 to retrieve the predictor models 322. The prediction module 216 may be further configured use the feature values extracted from the image data 404 as input to the first predictor model for psychometry prediction (as represented by block 708). The psychometry prediction may yield predicted psychometric features 710 as output. The prediction module 216 may be configured to use the feature values extracted from the image data 404 and the predicted psychometric features 710 as input to the third predictor model for predicting the business outcomes (as represented by block 712). The predicted business outcomes may be relevant to the target user 110 and/or an organization as described in FIG. 4. The application server 106 may be configured to store the predicted business outcomes in the external database server 108.

Figure 8A:
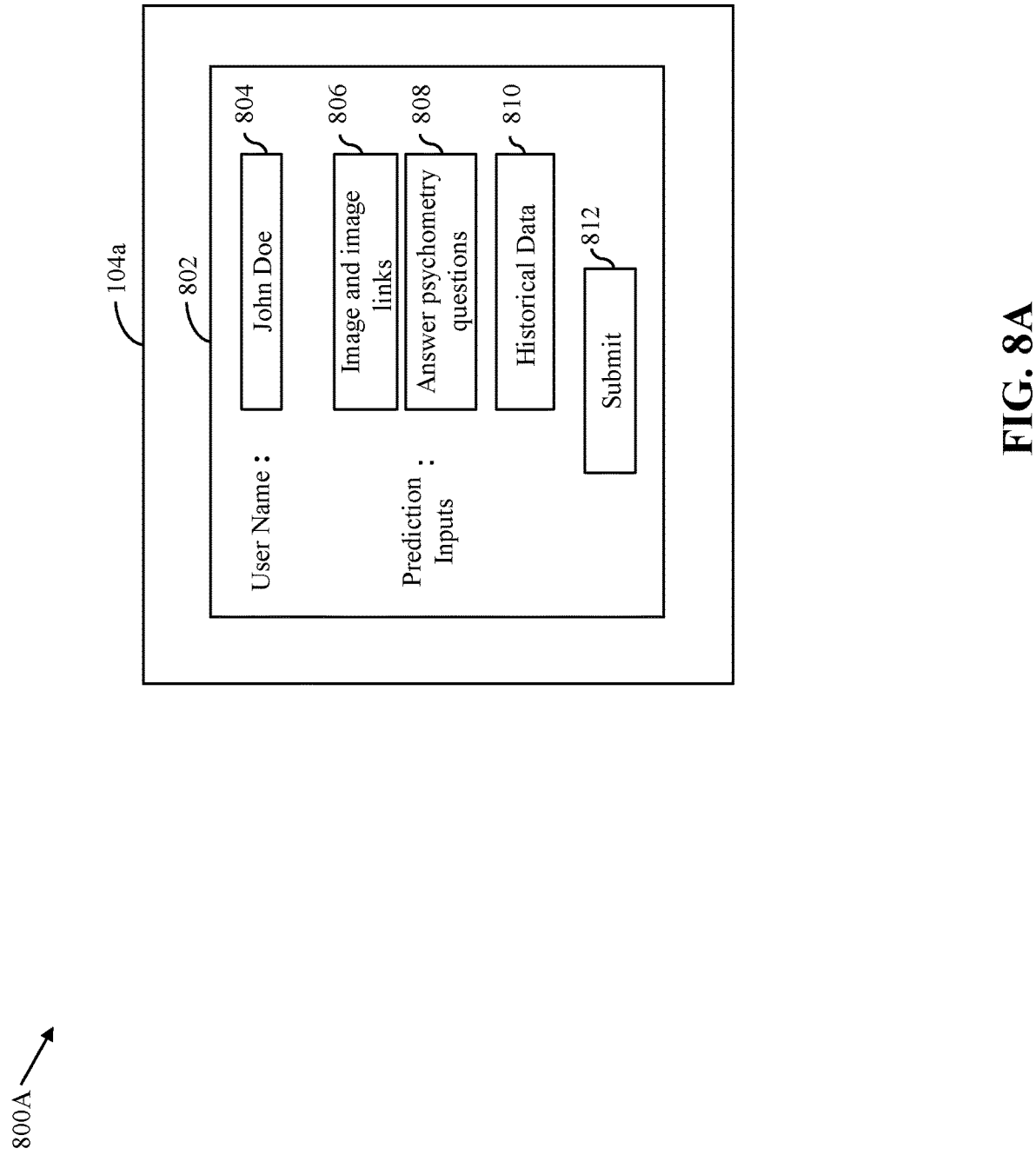
FIG. 8A is a block diagram that illustrates a user interface (UI) rendered on a test-user device by the application server for receiving sample data of a test user, in accordance with an embodiment of the disclosure.

FIG. 8A is block diagram 800A that illustrates a UI 802 rendered on the test-user device 104a by the application server 106 for retrieving the sample data 302 of the test user 102a, in accordance with an embodiment of the disclosure. The UI 802 may include a first input box 804, where a name is to be entered by the test user 102a (for example, "John Doe"). The UI 802 may further include first through third options 806-810 pertaining to inputs (i.e., the sample data 302) required from the test user 102a. The first through third options 806-810 may be selectable by the test user 102a. If the first option 806 is selected by the test user 102a, the application server 106 may be configured to retrieve images or URLs of images that are of interest to the test user 102a. If the second option 808 is selected by the test user 102a, the application server 106 may be configured to retrieve the answers 308 provided by the test user 102a to the psychometric questions. If the third option 810 is selected by the test user 102a, the application server 106 may be configured to retrieve the historical data 306 of the test user 102a. The retrieval of the images or the URLs of images that are of interest to the test user 102a, the answers 308 provided by the test user 102a to the psychometric questions, and the historical data 306 have been described in FIG. 3. The UI 802 may further include a submit button 812, which may be selected by the test user 102a to submit the sample data 402 to the application server 106.

It will be apparent to a person of ordinary skill in the art that the UI 802 is shown for illustrative purposes and should not be construed to limit the scope of the disclosure. In another embodiment, the application server 106 may render the UI 802 on the target-user device 112 for retrieving the target data (such as the target data 402, 502, 602, or 702) of the target user 110. The target user 110 may have an option to select any of the second and third options 808 and 810 whereas the first option 806 may be selected by default. The application server 106 may be configured to retrieve the target data (as described in FIGS. 4-7) based on the selection performed by the target user 110. For example, if the second option 808 is not selected by the target user 110 and the third option 810 is selected by the target user 110, the application server 106 may be configured to retrieve only the image data 404 and the historical data 406 of the target user 110.

Figure 8B:
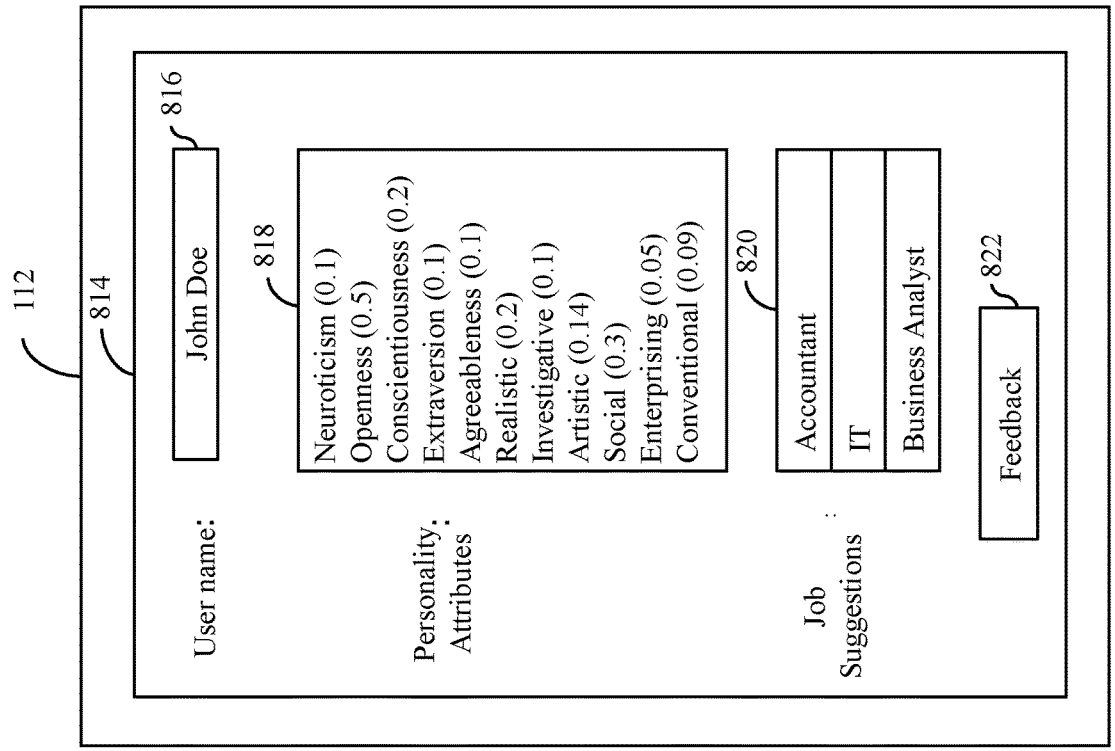
FIG. 8B is a block diagram that illustrates a UI rendered on a target-user device by the application server for presenting predicted business outcomes, in accordance with an embodiment of the disclosure.

FIG. 8B is a block diagram 800B that illustrates a UI 814 rendered on the target-user device 112 by the application server 106 for presenting predicted business outcomes, in accordance with an embodiment of the disclosure. The UI 814 may include a first field 816, where the name of the target user 110 may be displayed (for example, "John Doe"). The UI 814 may further include a first table 818 that may display personality attributes of the target user 110 and corresponding confidence scores. For example, the personality attributes of the target user 110 may be neuroticism, openness, conscientiousness, extraversion, agreeableness, realistic, investigative, artistic, social, enterprising, and conventional attributes having the confidence scores as 0.1, 0.5, 0.2, 0.1, 0.1, 0.2, 0.1, 0.14, 0.3, 0.05, and 0.09, respectively. The UI 814 may further include a second table 820 that may display various job suggestions (such as Accountant, IT, and Business analyst) for the target user 110. Likewise, the UI 814 may include additional tables (not shown) that may display relevant business outcomes, such as product purchase suggestions, travel suggestions, and the like, to the target user 110. The UI 814 may further include a feedback button 822. The target user 110 may select the feedback button 822 for providing a feedback, such as a score for each business outcome or a collective score, to the application server 106 indicating the relevance of the predicted business outcomes displayed in the second table 820 as a common or individual score per business outcome.

Figure 9A:
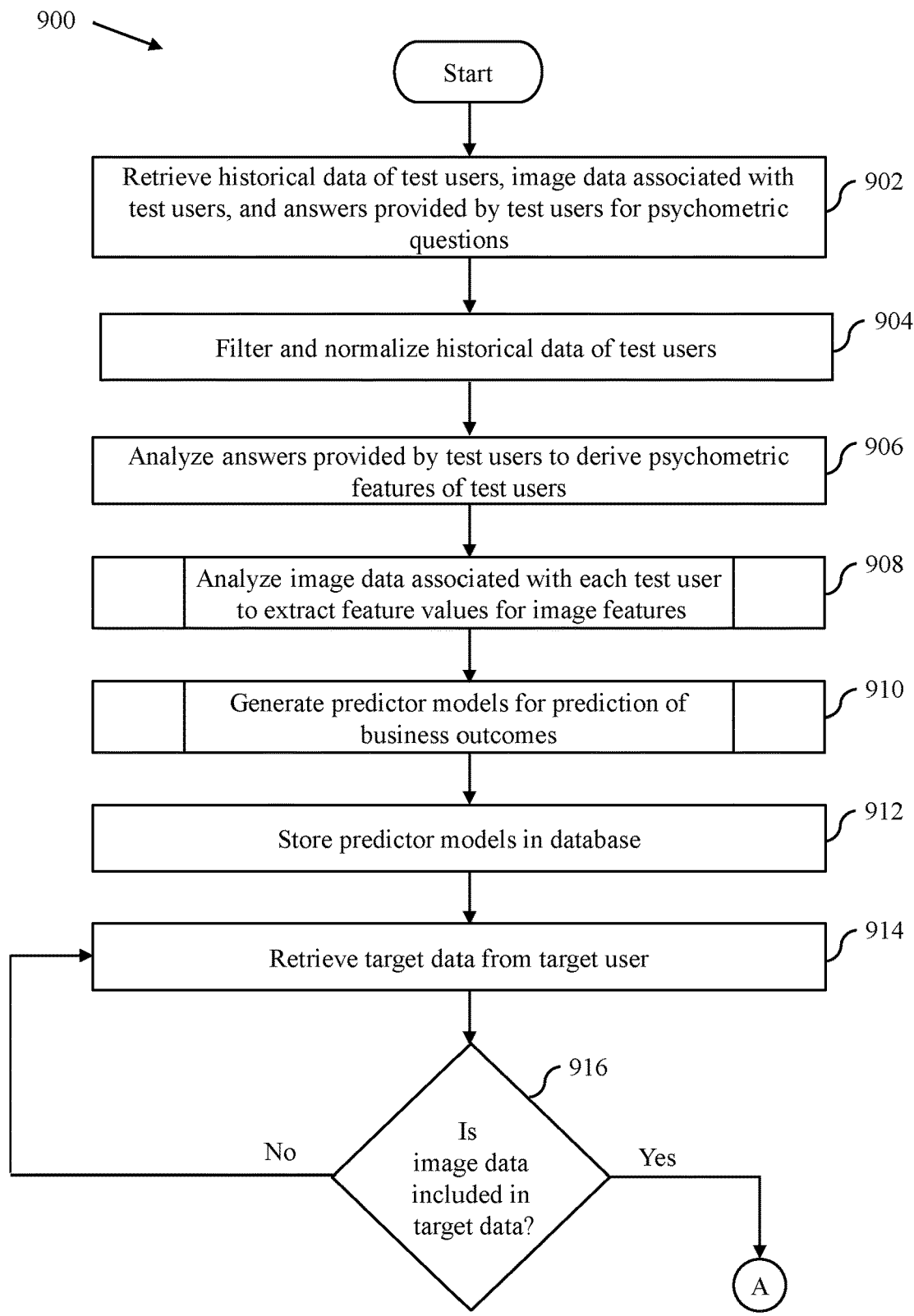
FIGS. 9A-9E, collectively represent a flow chart that illustrates a method for predicting business outcomes, in accordance with an embodiment of the disclosure.
Figure 9B:
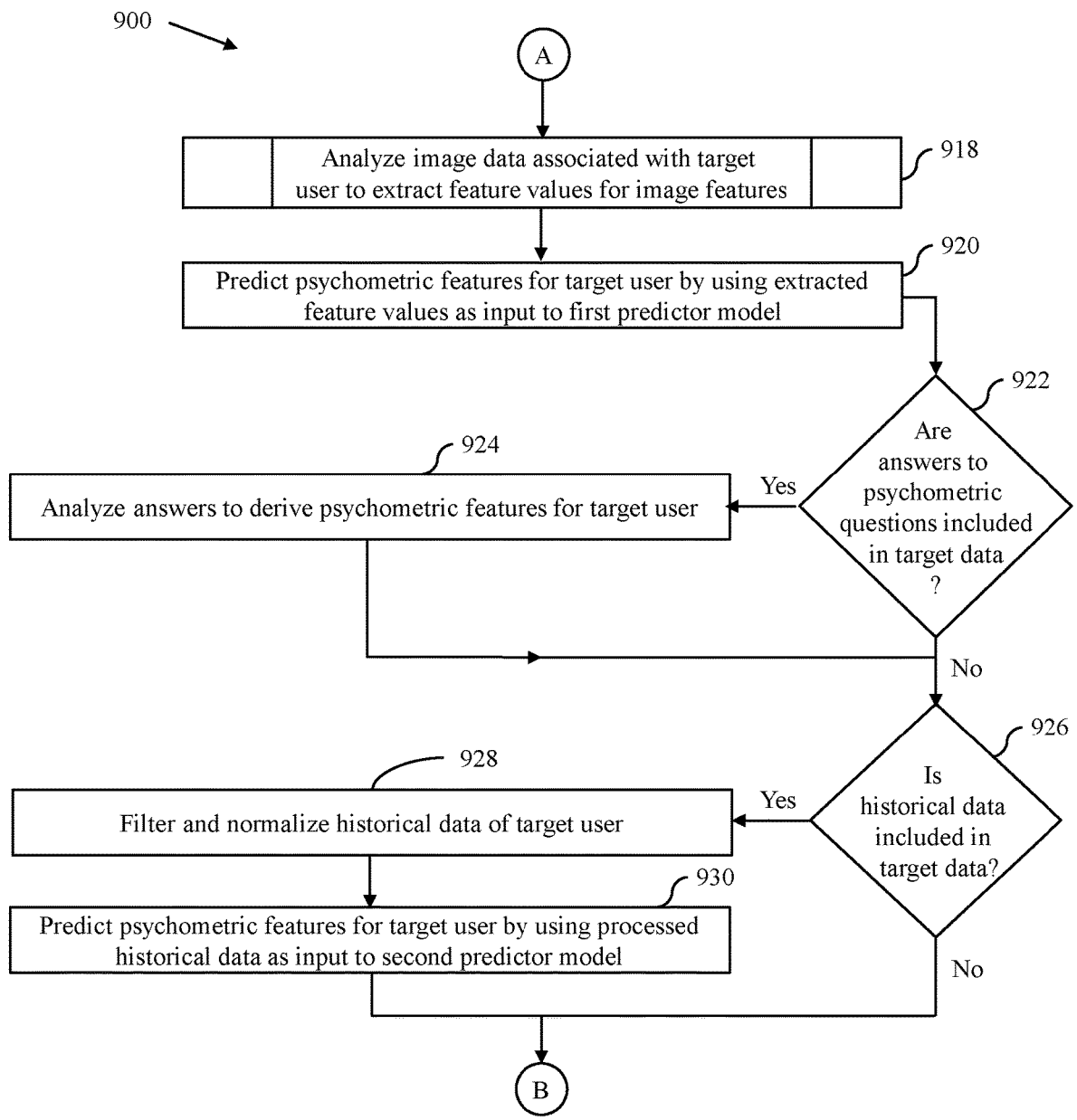
Figure 9C:
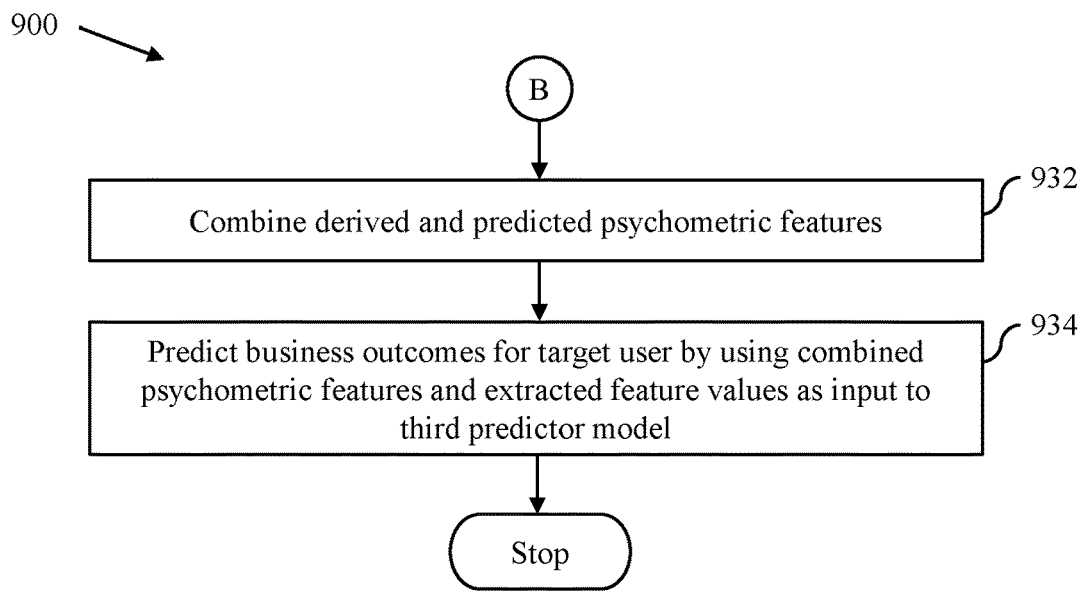

FIGS. 9A-9E, collectively represent a flow chart 900 that illustrates a method for predicting business outcomes, in accordance with an embodiment of the disclosure. Referring now to FIGS. 9A-9C, at 902, the historical data 306 the test users 102, the answers 308 provided by the test users 102 to the psychometric questions, and the image data 304 associated with the test users 102 (i.e., the sample data 302 as described in FIG. 3), are retrieved. The application server 106 may be configured to retrieve the historical data 306, the image data 304, and the answers 308. At 904, the historical data 306 of the test users 102 is filtered and normalized (as described in FIG. 3). At 906, the answers 308 provided by the test users 102 are analyzed for deriving the psychometric features of the test users 102 (as described in FIG. 3). At 908, the image data 304 associated with each test user 102 is analyzed for extracting feature values for the image features. The application server 106 may be configured to analyze the image data 304 by selecting one item at a time from the image data 304.

Figure 9D:
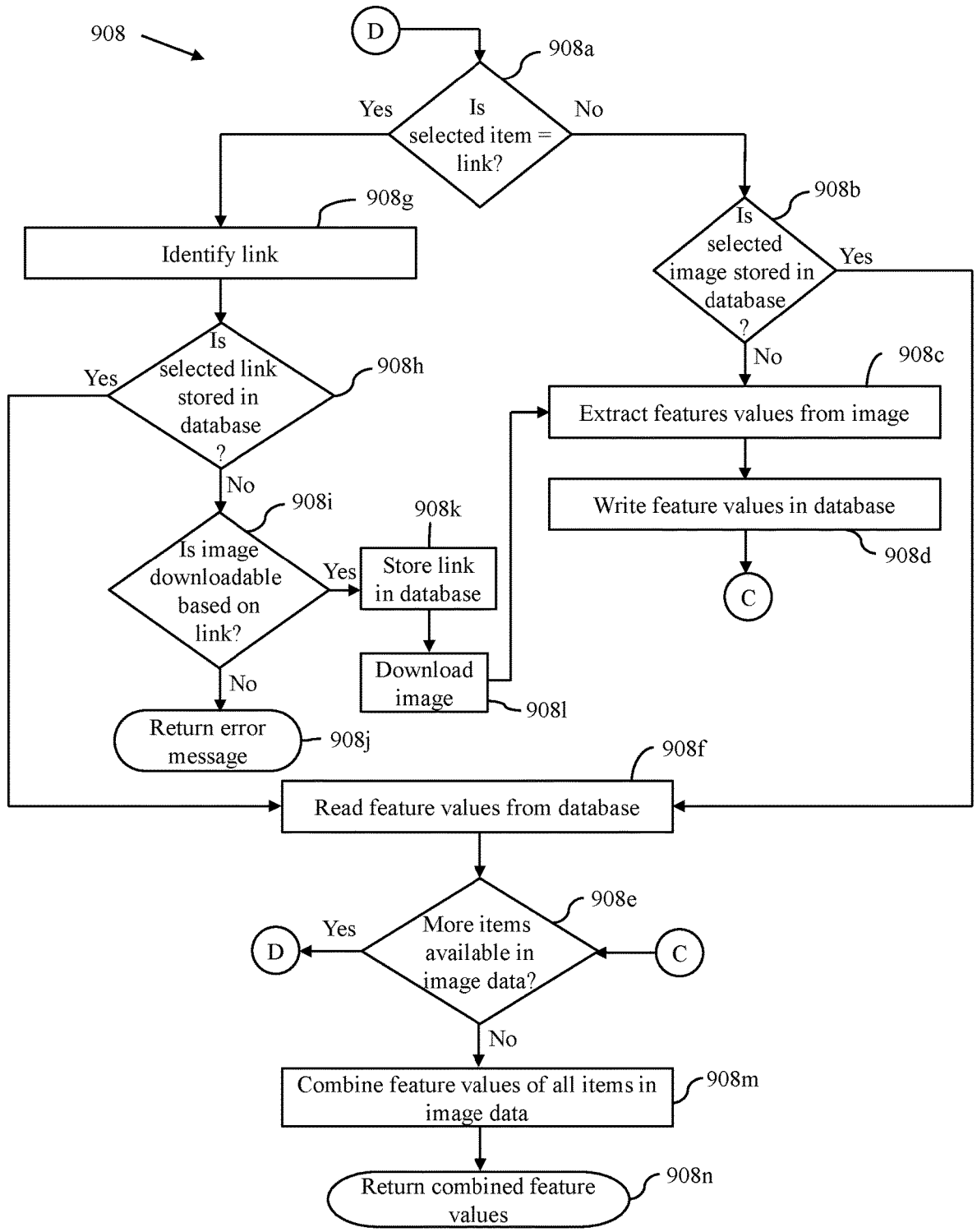

Referring now to FIG. 9D, at 908a, it is determined whether the selected item is a link (for example a URL or a web addresses). The link may not be suitable for image processing. If at 908a, it is determined that the selected item is an image and not a link, and control passes to 908b. At 908b, it is determined whether the selected image is stored in the external database server 108. If at 908b, it is determined that the selected image is not stored in the external database server 108, control passes to 908c. At 908c, feature values are extracted from the image (as described in FIG. 3). The feature values are extracted from the image corresponds to the object agnostic image features. At 908d, the feature values are written to the external database server 108. At 908e, it is determined whether the image data 304 includes more items. If at 908e, it is determined that the image data 304 includes more items that are not processed yet, control passes to 908a again. If at 908b, it is determined that the selected image is stored in the external database server 108, control passes to 908f. At 908f, the feature values are read from the external database server 108, and control passes to 908e.

If at 908a, it is determined that the selected item is a link, control passes to 908g. At 908g, the selected link is identified. The selected link may be a URL or a web address which is not suitable for image processing. At 908h, it is determined whether the selected link is stored in the external database server 108. If at 908h, it is determined that the selected link is stored in the external database server 108, control passes to 908f. If at 908h, it is determined that the selected link is not stored in the external database server 108, control passes to 908i. At 908i, it is determined whether it is possible to download an image based on the selected link. If at 908i, it is determined that the image is not downloadable, control passes to 908j. At 908j, an error message is returned. The error message indicates a failure to download the image based on the selected link and control passes to 908e. If at 908i, it is determined that the image is downloadable based on the selected link, control passes to 908k. At 908k, the link is stored in the external database server 108. At 908l, the image is downloaded. The application server 106 may download the image by using the link and control passes to 908c.

If at 908e, it is determined that all the items of the image data 304 are analyzed, control passes to 908m. At 908m, the feature values corresponding to all items (images and/or links) in the image data 304 are combined. At 908n, the combined feature values are returned and the control passes to 910.

Referring back to FIGS. 9A-9C, at 910, the predictor models 322 for prediction of business outcomes are generated (as described in FIG. 3). The application server 106 may be configured to use the combined feature values extracted from the image data 304, the analyzed historical data 306, and the derived psychometric features to generate the predictor models 322.

Figure 9E:
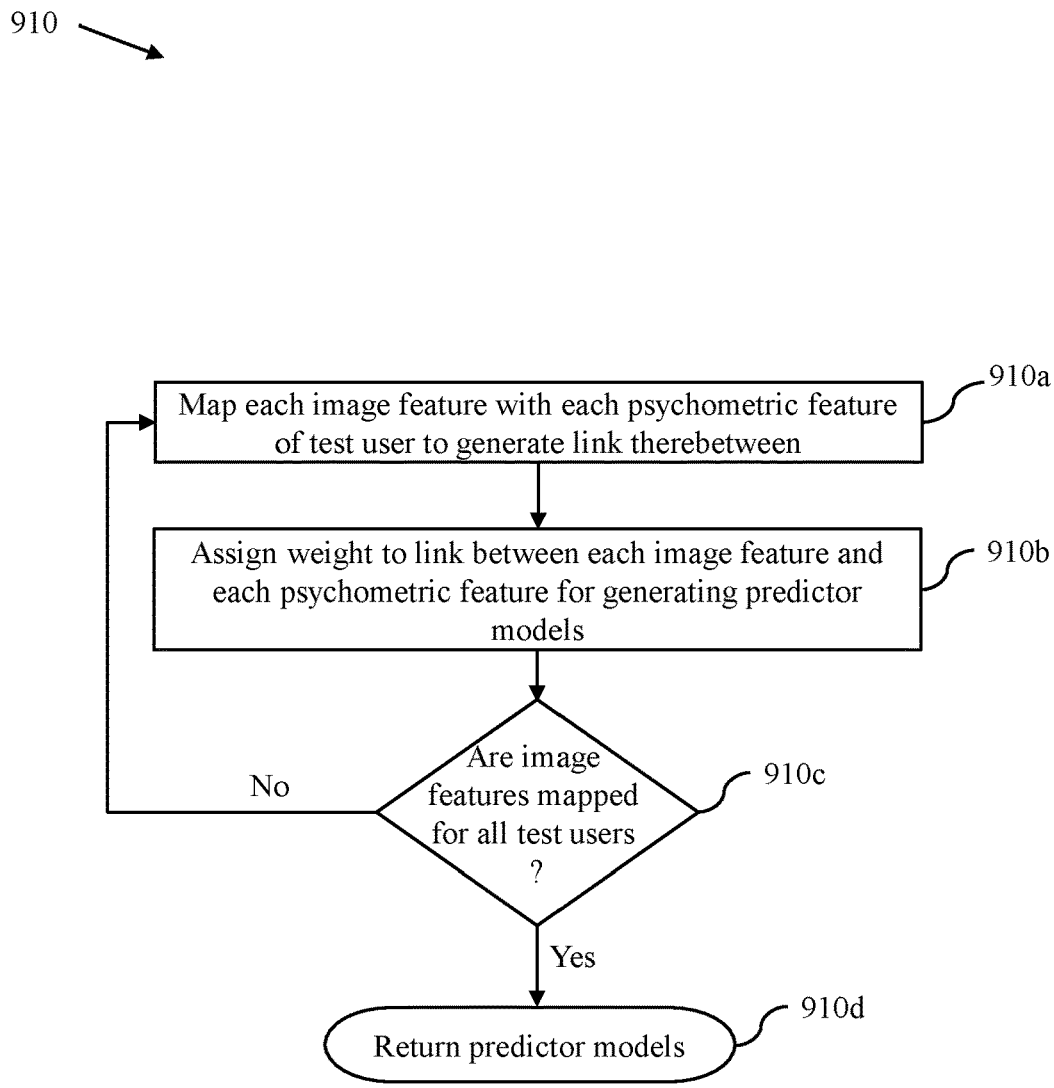

Referring now to FIG. 9E, at 910a, each image feature is mapped with each psychometric feature of a test user (e.g., any test user 102) to generate link therebetween. The application server 106 may be configured to map each image feature with a confidence score of each psychometric feature derived for the test user (e.g., any test user 102). At 910b, a weight is assigned to the link between each image feature and each psychometric feature for generating the predictor models 322. The application server 106 may be configured to assign the weight based on the extracted feature values. At 910c, it is determined whether the image features are mapped for all the test users 102. If at 910c, it is determined that the image features are not mapped for all the test users 102, control passes to 910c. The application server 106 may be configured to perform 910a-910c until the image features are mapped for all the test users 102. If at 910c, it is determined that image features are mapped for all the test users 102, control passes to 910d. At 910d, the predictor models 322 are returned to the application server 106.

Referring back to FIGS. 9A-9C, at 912, the generated predictor models 322 are stored in the external database server 108. At 914, the target data is retrieved from the target user 110. At 916, it is determined whether the target data (such as the target data 402, 502, 602, or 702) includes the image data 404. If at 916, it is determined that the target data does not include the image data 404, control passes to 914. The application server 106 may be configured to perform 914 again until the image data 404 of the target user 110 is retrieved. If at 916, it is determined that the target data includes the image data 404, control passes to 918. At 918, the image data 404 associated with the target user 110 is analyzed for extracting feature values for the image features. The process of extracting feature values from the image data 404 is same as that performed for the image data 304 of the test users 102 comprising 908a-908n of FIG. 9D. At 920, the psychometric features of the target user 110 are predicted by using extracted feature values as input to the first predictor model.

At 922, it is determined whether the target data of the target user 110 includes the answers 408 to the psychometric questions. If at 922, it is determined that the target data includes the answers 408 provided by the target user 110, control passes to 924. At 924, the answers 408 are analyzed for deriving the psychometric features of the target user 110 (as described in FIG. 4). If at 922, it is determined that the target data does not include the answers 408, control passes to 926. At 926, it is determined whether the target data includes the historical data 406. If at 926, it is determined that the target data includes the historical data 406 of the target user 110, control passes to 928. At 928, the historical data 406 of the target user 110 is filtered and normalized. At 930, the psychometric features for the target user 110 are predicted by using the processed historical data 406 as input to the second predictor model. Control passes to 932. If at 926, it is determined that the target data does not include the historical data 406, control passes to 932. At 932, the derived and predicted psychometric features are combined. At 934 the business outcomes for the target user 110 are predicted by using the combined psychometric features and the extracted feature values as input to the third predictor model.

Figure 10:
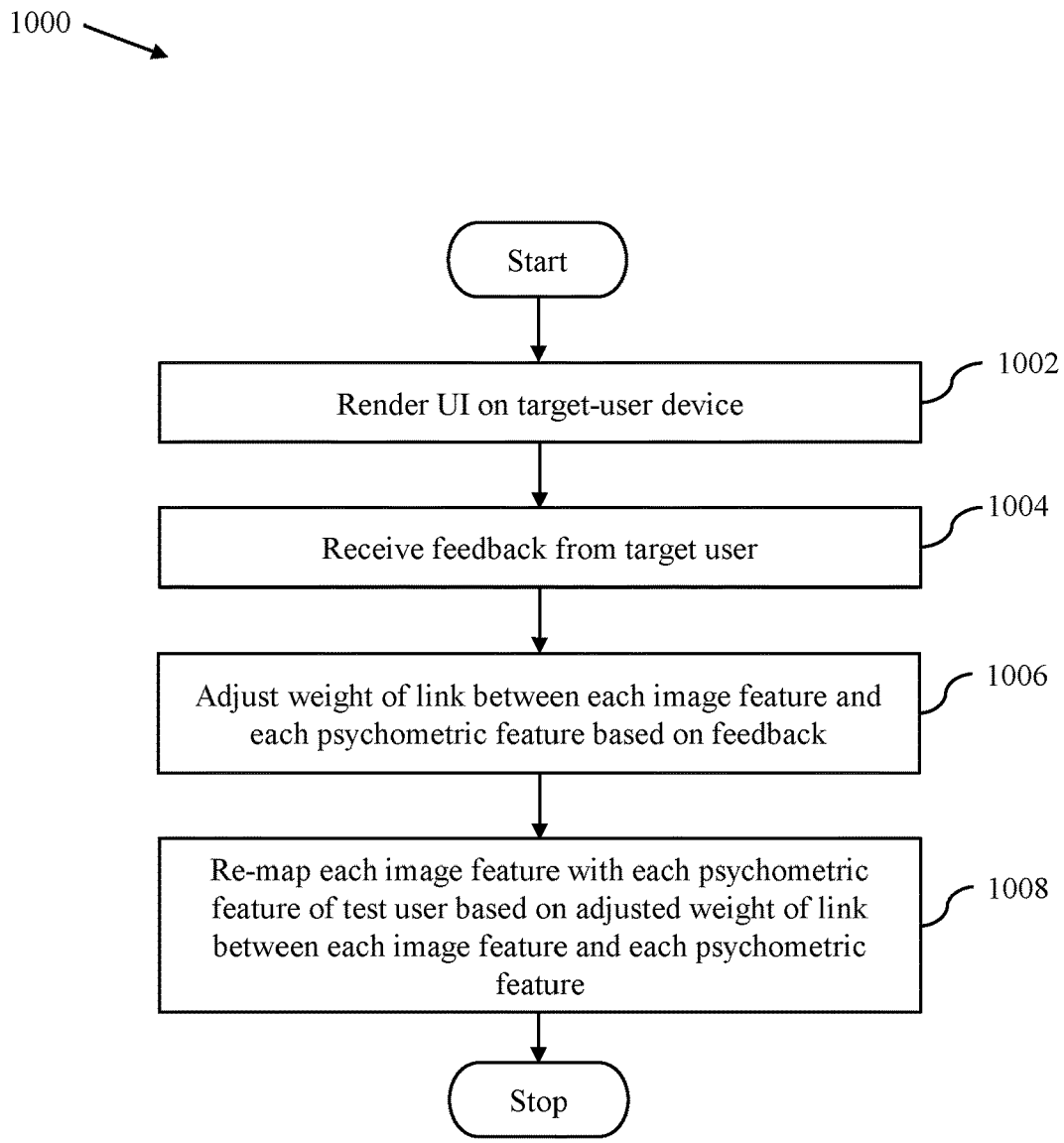
FIG. 10 is a flow chart that illustrates a method for updating the predictor models, in accordance with an embodiment of the disclosure.

FIG. 10 is a flow chart 1000 that illustrates a method for updating the predictor models 322, in accordance with an embodiment of the disclosure. At 1002, the UI 814 is rendered on the target-user device 112. The application server 106 may be configured to render the UI 814 to present the predicted business outcomes and predicted psychometric features (e.g., the personality attributes) to the target user 110. At 1004, a feedback is received from the target user 110. The application server 106 may be configured to receive the feedback indicating relevancy of the predicted business outcomes and the predicted psychometric features from the target user 110. At 1006, the weight assigned of the link between each image feature and each psychometric feature is adjusted based on the feedback. The application server 106 may be configured to increase or decrease the weight based on a positive or negative feedback from the target user 110. At 1008, each image feature is re-mapped with each psychometric feature of the test user 102a based on the adjusted weight of the link between each image feature and each psychometric feature.

Figure 11:
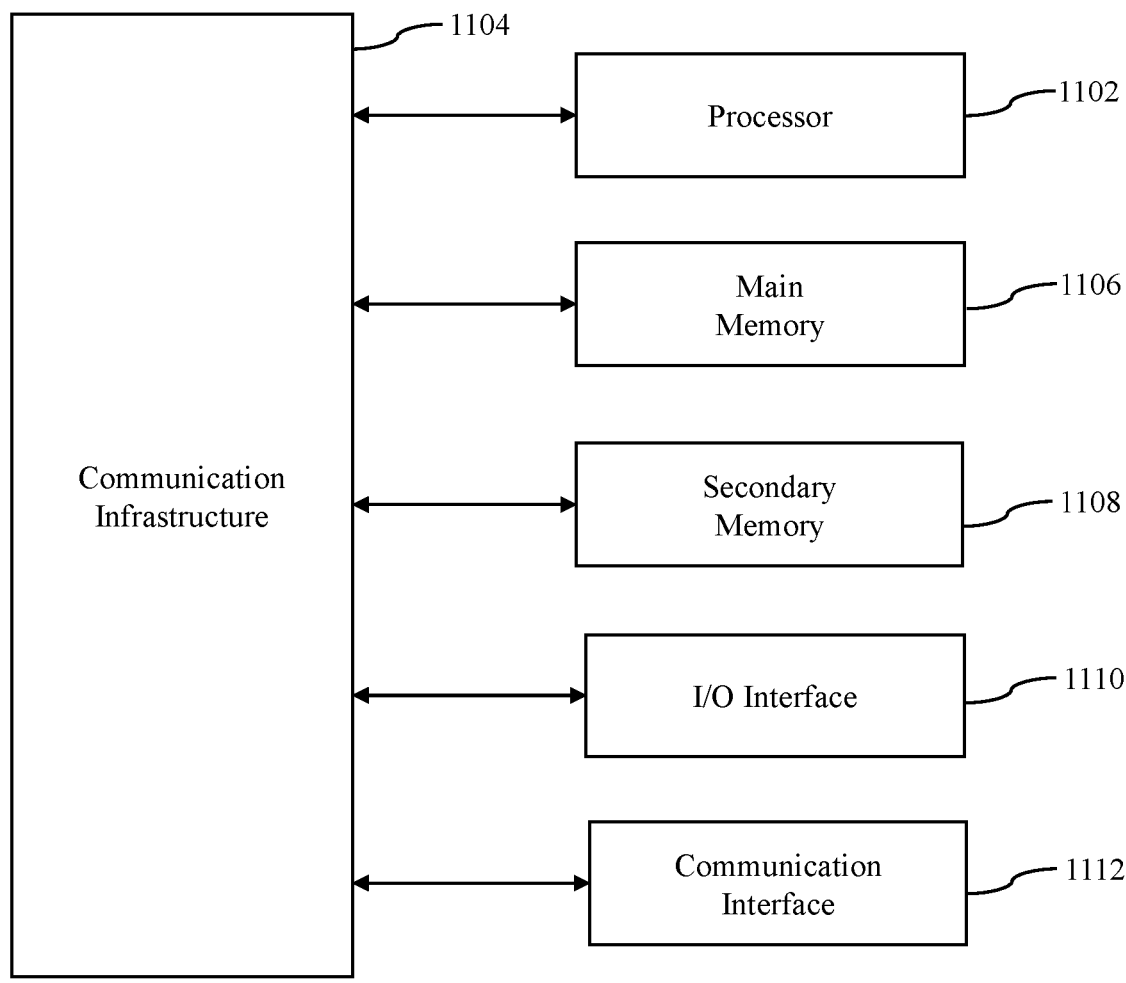
FIG. 11 is a block diagram that illustrates system architecture of a computer system, in accordance with an embodiment of the disclosure.

FIG. 11 is a block diagram that illustrates system architecture of a computer system 1000, in accordance with an embodiment of the disclosure. An embodiment of the disclosure, or portions thereof, may be implemented as computer readable code on the computer system 1100. In one example, the test-user and target-user devices 104 and 112 and the external database server 108 of FIG. 1 may be implemented in the computer system 1100 using hardware, software, firmware, non-transitory computer readable media having instructions stored thereon, or a combination thereof and may be implemented in one or more computer systems or other processing systems. Hardware, software, or any combination thereof may embody modules and components used to implement the method of FIGS. 9A-9E and 10.

The computer system 1100 may include a processor 1102 that may be a special-purpose or a general-purpose processing device. The processor 1102 may be a single processor, multiple processors, or combinations thereof. The processor 1102 may have one or more processor cores. In one example, the processor 1102 is an octa-core processor. The processor 1102 may be further connected to a communication infrastructure 1104, such as a bus, message queue, multi-core message-passing scheme, and the like. The computer system 1100 may further include a main memory 1106 and a secondary memory 1108. Examples of the main memory 1106 may include RAM, ROM, and the like. The secondary memory 1108 may include a hard disk drive or a removable storage drive, such as a floppy disk drive, a magnetic tape drive, a compact disk, an optical disk drive, a flash memory, and the like. The removable storage drive may further read from and/or write to a removable storage device in a manner known in the art. In one example, if the removable storage drive is a compact disk drive, the removable storage device may be a compact disk. In an embodiment, the removable storage unit may be a non-transitory computer readable recording media.

The computer system 1100 may further include an input/output (I/O) interface 1110 and a communication interface 1112. The I/O interface 1110 may include various input and output devices that are configured to communicate with the processor 1102. Examples of the input devices may include a keyboard, a mouse, a joystick, a touchscreen, a microphone, and the like. Examples of the output devices may include a display screen, a speaker, headphones, and the like. The communication interface 1112 may be configured to allow data to be transferred between the computer system 1100 and various devices that are communicatively coupled to the computer system 1100. Examples of the communication interface 1112 may include a modem, a network interface, i.e., an Ethernet card, a communication port, and the like. Data transferred via the communication interface 1112 may correspond to signals, such as electronic, electromagnetic, optical, or other signals as will be apparent to a person skilled in the art. The signals may travel via a communication channel (not shown) which may be configured to transmit the signals to devices that are communicatively coupled to the computer system 1100. Examples of the communication channel may include, but are not limited to, cable, fiber optics, a phone line, a cellular phone link, a radio frequency link, and the like. The main memory 1106 and the secondary memory 1108 may refer to non-transitory computer readable mediums that may provide data that enables the computer system 1100 to implement the method illustrated in FIGS. 9A-9E and 10.

Various embodiments of the present disclosure include the application server 106 for predicting business outcomes for the target user 110. The application server 106 may retrieve the historical data 306 the test users 102, images 304 that are of interest to the test users 102, and the answers 308 provided by the test users 102 to a set of psychometric questions. The first processor 202 analyze the answers 308 and the second processor 304 may analyze the images 304. The answers 308 are analyzed for deriving one or more psychometric features (as represented by block 318 in FIG. 3) of the test users 102. The images 304 are analyzed for extracting a first set of feature values corresponding to a set of image features from the images 304. Each image feature of the set of image features is independent of one or more objects associated with the images 304. The model generator 212 may generate the predictor models 322 based on the historical data 306 of the test users 102, the first set of feature values, and the one or more psychometric features of the test users 102. The prediction module 216 may predict one or more business outcomes for the target user 110 based on the one or more predictor models 322 and images 404 that are of interest to the target user 110.

In one embodiment, a non-transitory computer readable medium having stored thereon, computer executable instructions, which when executed by a computer, cause the computer to execute operations for predicting business outcomes for the target user 110 (as described in FIGS. 9A-9E). The operations include retrieving the historical data 306 of at least one test user (for example, the test user 102a), a first set of images (i.e., the image data 304) that is of interest to the test user 102a, and a first set of answers 308 provided by the test user 102a to a set of psychometric questions. The operations further include analyzing the first set of answers 308 and the first set of images 304 by the first and second processors 202 and 204, respectively. The first set of answers 308 is analyzed for deriving one or more psychometric features (as represented by block 318 in FIG. 3) of the test user 102a. The first set of images 304 is analyzed for extracting a first set of feature values corresponding to a set of image features from the first set of images 304. Each image feature of the set of image features is independent of one or more objects associated with the first set of images. The operations further include generating the predictor models 322, by the model generator 212, based on the historical data 306 of the test user 102a, the first set of feature values, and the one or more psychometric features of the test user 102a. The operations further include predicting one or more business outcomes for the target user 110, by the prediction module 216, based on the predictor models 322 and a second set of images (i.e., the image data 404) that is of interest to the target user 110.

Various embodiments of the disclosure include the application server 106 which may enable prediction of business outcomes by analyzing image interests of the target user 110. The image interests of the target user 110 may accurately reflect the subconscious mind of the target user 110 at any given time instance. The predictor models 322 generated by the application server 106 are trained based on the sample data 302 of multiple test users 102. The sample data 302 includes the image data 304, the historical data 306, and the answers 308 provided by the test users 102, which reflects the subconscious mind of the test users 102. Due to chronological processing of the image data 404 based on the date and time markers, behavioral changes exhibited by the target user 110 over a period of time may be accurately monitored. Image interests of the target user 110 in the past and image interests of the target user 110 in the present are direct indicators of the behavioral changes the target user 110 is going through. As the subconscious mind is responsible for majority of decision making and directly related to the psychometric orientation, the prediction accuracy of the predictor models 322 is very high. Thus, the disclosure yields more accurate results in comparison to the related techniques. The ability of the predictor models 322 to accurately predict psychometric orientation and business outcomes may provide competitive edge to a service company, utilizing the predictor models 322, over its competitors. For example, the service company may utilize technological improvements of the predictor models 322 to provide targeted services to the customers. Similarly, the technological improvements provided by the predictor models 328 enables an organization to keep track of behavioral changes and mental health of corresponding employees by periodically analyzing employees' image interests, rather than hire a psychiatrist or conduct time consuming psychometric tests. The technological improvements provided by the predictor models 322 may be utilized to concurrently predict business outcomes for multiple target users, thereby reducing the time spent by organizations on data analytics for various operations, such as hiring, or the like. The disclosure has applicability in, and provides improvements in technologies that are customer and employee centric. For example, e-commerce industries, business ventures, customer helpdesks, or the like.

A person of ordinary skill in the art will appreciate that embodiments and exemplary scenarios of the disclosed subject matter may be practiced with various computer system configurations, including multi-core multiprocessor systems, minicomputers, mainframe computers, computers linked or clustered with distributed functions, as well as pervasive or miniature computers that may be embedded into virtually any device. Further, the operations may be described as a sequential process, however some of the operations may in fact be performed in parallel, concurrently, and/or in a distributed environment, and with program code stored locally or remotely for access by single or multiprocessor machines. In addition, in some embodiments the order of operations may be rearranged without departing from the spirit of the disclosed subject matter.

Techniques consistent with the disclosure provide, among other features, systems and methods for predicting business outcomes. While various exemplary embodiments of the disclosed system and method have been described above it should be understood that they have been presented for purposes of example only, not limitations. It is not exhaustive and does not limit the disclosure to the precise form disclosed. Modifications and variations are possible in light of the above teachings or may be acquired from practicing of the disclosure, without departing from the breadth or scope.

While various embodiments of the disclosure have been illustrated and described, it will be clear that the disclosure is not limited to these embodiments only. Numerous modifications, changes, variations, substitutions, and equivalents will be apparent to those skilled in the art, without departing from the spirit and scope of the disclosure, as described in the claims.

What is claimed is:

1. A method for predicting business outcomes for users, the method comprising:
   retrieving, by a server, historical data of at least one test user, a first set of answers provided by the test user to a set of psychometric questions, and a first set of images that is of interest to the test user;
   analyzing, by the server, the first set of answers to derive one or more psychometric features of the test user;
   converting, by the server using an image processor, each of the first set of images to a defined resolution format;
   extracting from each of the converted first set of images, by the server, a first set of feature values for a set of image features, wherein the set of image features is independent of one or more objects associated with each of the converted first set of images and includes at least a color distribution, and wherein a first subset of the first set of feature values indicates the color distribution for a first set of colors present in each of the first set of images;
   generating, by the server, one or more predictor models based on an association between the historical data of the test user, the one or more psychometric features of the test user, and the set of image features, wherein the association between the one or more psychometric features of the test user and the set of image features is determined based on the first set of feature values;
   retrieving, by the server, a second set of images that is of interest to a target user, wherein each image of the second set of images is associated with a corresponding date and time marker indicating when an interest was shown in the corresponding image by the target user;
   converting, by the server using the image processor, each of the second set of images to the defined resolution format;
   extracting from each of the converted second set of images, by the server, a second set of feature values for the set of image features, wherein a second subset of the second set of feature values indicates the color distribution for a second set of colors present in each of the converted second set of images, wherein the second set of feature values are extracted from each converted image of the converted second set of images based on a chronological order associated with each image of the second set of images, and wherein the chronological order associated with each image of the second set of images is indicated by the corresponding date and time marker; and predicting, by the server, one or more business outcomes for the target user based on at least the one or more predictor models and the second set of feature values.

2. The method of claim 1, wherein the one or more business outcomes include product purchase affinity and purchase behavior of the target user, and compatibility match, color affinity, employment affinity, and employment suggestions for the target user.

3. The method of claim 1, wherein the set of image features further includes a set of curves, a set of perspective markers, semantics, and tonality.

4. The method of claim 1, wherein the historical data includes one or more job details, education particulars, a purchase history, a travel history, one or more activities on social media platforms, and one or more likes and dislikes of the test user.

5. The method of claim 1, further comprising predicting, by the server, one or more psychometric features of the target user based on the second set of feature values, wherein the predicted one or more psychometric features of the target user are further used as input to the one or more predictor models for predicting the one or more business outcomes.

6. The method of claim 1, further comprising analyzing, by the server, a second set of answers provided by the target user to the set of psychometric questions to derive one or more psychometric features of the target user, wherein the one or more psychometric features of the target user are further used as input to the one or more predictor models for predicting the one or more business outcomes.

7. The method of claim 1, further comprising:
mapping, by the server, each image feature of the set of image features to each psychometric feature of the test user based on the first set of feature values for generating a link therebetween; and
assigning, by the server, a weight to the link between each image feature of the set of image features and each psychometric feature of the test user for generating the one or more predictor models, wherein the assigned weight is indicative of the association between each of the one or more psychometric features of the test user and each of the set of image features.

8. The method of claim 7, further comprising:
rendering, by the server on a user device of the target user, a user interface to present the one or more business outcomes to the target user; and
receiving, by the server, a feedback provided by the target user on the one or more business outcomes, wherein the feedback is provided by way of the user interface.

9. The method of claim 8, further comprising adjusting, by the server, the weight of the link between each image feature of the set of image features and each psychometric feature of the test user based on the feedback provided by the target user for updating the one or more predictor models.

10. The method of claim 1, further comprising determining, by the server, one or more behavioral changes exhibited by the target user over a time period based on the chronological extraction from each image of the second set of images, wherein the one or more business outcomes are further predicted based on the one or more behavioral changes of the target user.

11. A system for predicting business outcomes for users, the system comprising:
a server including circuitry that is configured to:
retrieve historical data of at least one test user, a first set of answers provided by the test user to a set of psychometric questions, and a first set of images that is of interest to the test user;
analyze the first set of answers to derive one or more psychometric features of test user;
convert each of the first set of images to a defined resolution format;
extract from each of the converted first set images a first set of feature values for a set of image features, wherein the set of image features is independent of one or more objects associated with each of the converted first set of images and includes at least a color distribution, and wherein a first subset of the first set of feature values indicates the color distribution for a first set of colors present in each of the converted first set of images;
generate one or more predictor models based on an association between the historical data of the test user, the one or more psychometric features of the test user, and the set of image features, wherein the association between the one or more psychometric features of the test user and the set of image features is determined based on the first set of feature values;
retrieve a second set of images that is of interest to a target user, wherein each image of the second set of images is associated with a corresponding date and time marker indicating when an interest was shown in the corresponding image by the target user;
convert each of the second set of images to the defined resolution format;
extract from each of the converted second set of images a second set of feature values for the set of image features, wherein a second subset of the second set of feature values indicates the color distribution for a second set of colors present in each of the converted second set of images, wherein the second set of feature values are extracted from each converted image of the converted second set of images based on a chronological order associated with each image of the second set of images, and wherein the chronological order associated with each image of the second set of images is indicated by the corresponding date and time marker; and
predict one or more business outcomes for the target user based on at least the one or more predictor models and the second set of feature values.

12. The system of claim 11, wherein the one or more business outcomes include product purchase affinity and purchase behavior of the target user, and compatibility match, color affinity, employment affinity, and employment suggestions for the target user, and wherein the set of image features further includes a set of curves, a set of perspective markers, semantics, and tonality.

13. The system of claim 11, wherein the historical data includes one or more job details, education particulars, a purchase history, a travel history, one or more activities on social media platforms, and one or more likes and dislikes of the test user.

14. The system of claim 11, wherein the circuitry is further configured to predict one or more psychometric features of the target user based on the second set of feature values and wherein the predicted one or more psychometric features of the target user are further used as input to the one or more predictor models for predicting the one or more business outcomes.

15. The system of claim 11, wherein the circuitry is further configured to analyze a second set of answers provided by the target user to the set of psychometric questions to derive one or more psychometric features of the target user, and wherein the one or more psychometric features of the target user are further used as input to the one or more predictor models for predicting the one or more business outcomes.

16. The system of claim 11, wherein the circuitry is further configured to:
   map each image feature of the set of image features to each psychometric feature of the test user based on the first set of feature values for generating a link therebetween; and
   assign a weight to the link between each image feature of the set of image features and each psychometric feature of the test user for generating the one or more predictor models, wherein the assigned weight is indicative of the association between each of the one or more psychometric features of the test user and each of the set of image features.

17. The system of claim 16, wherein the circuitry is further configured to:
   render, on a user device of the target user, a user interface to present for the one or more business outcomes to the target user; and
   receive a feedback provided by the target user on the one or more business outcomes, wherein the feedback is provided by way of the user interface.

18. The system of claim 17, wherein the circuitry is further configured to adjust the weight of the link between each image feature of the set of image features and each psychometric feature of the test user based on the feedback provided by the target user for updating the one or more predictor models.

19. A non-transitory computer readable medium having stored thereon, computer executable instructions, which when executed by a computer, cause the computer to execute operations, the operations comprising:
   retrieving historical data of at least one test user, a first set of answers provided by the test user to a set of psychometric questions, and a first set of images that is of interest to the test user;
   analyzing the first set of answers to derive one or more psychometric features of the test users;
   converting each of the first set of images to a defined resolution format;
   extracting from each of the converted first set of images a first set of feature values for a set of image features, wherein the set of image features is independent of one or more objects associated with each of the converted first set of images and include at least a color distribution, and wherein a first subset of the first set of feature values indicates the color distribution for a set of colors present in each of the converted first set of images;
   generating one or more predictor models based on an association between the historical data of the test user, the one or more psychometric features of the test user, and the set of image features, wherein the association between the one or more psychometric features of the test user and the set of image features is determined based on the first set of feature values;
   retrieving a second set of images that is of interest to a target user, wherein each image of the second set of images is associated with a corresponding date and time marker indicating when an interest was shown in the corresponding image by the target user;
   converting each of the second set of images to the defined resolution format;
   extracting from each of the converted second set of images a second set of feature values corresponding to the set of image features, wherein a second subset of the second set of feature values indicates the color distribution for a second set of colors present in each of the converted second set of images, wherein the second set of feature values are extracted from each converted image of the converted second set of images based on a chronological order associated with each image of the second set of images, and wherein the chronological order associated with each image of the second set of images is indicated by the corresponding date and time marker; and
   predicting one or more business outcomes for the target user based on at least the one or more predictor models and the second set of feature values.

\* \* \* \* \*